US007094878B2

(12) United States Patent
Lee et al.

(10) Patent No.: US 7,094,878 B2
(45) Date of Patent: Aug. 22, 2006

(54) AORTIC CARBOXYPEPTIDASE-LIKE POLYPEPTIDE

(75) Inventors: Mu-En Lee, Newton, MA (US); Matthew D. Layne, Brighton, MA (US); Shaw-Fang Yet, Andover, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 709 days.

(21) Appl. No.: 10/238,876

(22) Filed: Sep. 10, 2002

(65) Prior Publication Data

US 2003/0084464 A1    May 1, 2003

Related U.S. Application Data

(60) Division of application No. 09/060,482, filed on Apr. 16, 1998, now Pat. No. 6,468,766, which is a continuation-in-part of application No. 08/818,009, filed on Mar. 14, 1997, now abandoned.

(60) Provisional application No. 60/013,439, filed on Mar. 15, 1996.

(51) Int. Cl.
    *C07K 14/47* (2006.01)
(52) U.S. Cl. .................................................. 530/350
(58) Field of Classification Search ..................... None
    See application file for complete search history.

(56) References Cited

U.S. PATENT DOCUMENTS 5,460,951 A    10/1995    Kawai et al.

FOREIGN PATENT DOCUMENTS

WO    WO/93/16178    8/1993

OTHER PUBLICATIONS

Alberts et al., "Molecular Biology of the Cell, Jan.", Garland Publishing, Inc., New York, NY, p. 119 (1994).
Ausubei et al., "Preparation and Analysis of DNA, Curr. Protocols in Mol. Biol.", 2.10.8-2.10.15.
Blanar et al., "Interaction Cloning: Identification of a Helix-loop-Helix Zipper Protein That Interacts With c-Fos", Science 256; 1014-1018 (1992).
Blaner et al., "Meso 1, a Basic-Helix-Loop-Helix Protein Involved in Mammailan Presomitic Mesoderm Development", PNAS USA 92:5870-5874 (1995).
Brendel et al., "Methods and Algorithms for Statistical Analysis of Protein Sequences", PNAS USA 89:2002-2006, (1992).
Cool et al., "Carboxypeptidase E is a Regulated Secretory Pathway Sorting Receptor: Genetic Obliteration Leads to Endocrine Disorders in Cpefat Mice". Cell 88:73-83 (1997).
Gerhard, "Fusion of Cells in Suspension and Outgrowth of Hybrids in Conditioned Medium", Monclonal Antibodies: Hybridomas: A New Dimension in Biological Analyses, Plenum Press. pp. 370-371 (1980).

Gunther et al., "Functional Angiotensin II Receptors in Cultered Vasuclar Smooth Muscle Cells", J. Cell Biol. 92:289-298, (1982).
He et al., "A Eurkyotic Transcriptial Repressor with Carboxypeptidase Activity", Nature 378:92-96 (1995).
He et al., "Neuropilin is a Receptor for the Axonal Chemorepellent Semaphorin III", Cell 90:739-751 (1997).
Hidai et al., "Cloning and Characterization of Development Endothelial Locus-1: An Emryonic Endothelial Cell Protein that Binds the αvβ3 Integrin Reeceptor", Genes & Development 12:21-33 (1998).
Hsieh et al., "APEG-1, a Novel Gene Preferentially Expressed in Aortic Smooth Muscle Cells, Is down-regulated by Vascular Injury", J. Biol. Chem. 271 (29):17354-17359 (1996).
"Human Molecular Genetics", BIOS Scientific Publishers Ltd. 9 Newtec Place, Magdalen Road, Oxford OX4 1RE, UK, A John Wiley & Sons, Inc. Publication, pp. 107-108, 114-119 (1996).
Itakura et al., "Synthesis and Use of Synthetic Oligonucleotides", Ann. Rev. Biochem., 53:323-356 (1984).
Ivaschenko et al., "A Deletion of Two Nucleotides in Exon 10 of the CFTR Gene in a Soviet Family with Cystic Fibrosis Causing Early Infant Death", Genomics. 10:298-299 (1991).
Jain et al., "In Vitor System for Differentiating Pluripotent Neural Crest Cells into Smooth Muscle Cells", J. Biol. Chem. 273(11):5993-5996 (1998).
Johnson et al., "A Receptor Tyrosine Kinase Found in Breast Carcinoma Cells has an Extracellural Discoidin I-Like Domain", PNAS USA 90:5677-5681 (1993).
Kane et al., "Cloning of a cDN Coding for Human Factor V, A Blood Coagulation Factor Homologous to Factor VIII and Ceruloplasmin", PNAS USA 83:6800-6804 (1986).
Kane et al., "Blood Coagulation Factors V and VIII Structural and Functional Similartiies and Their Relationship to Hemorrhagic and Thrombotic Disorders", J. Amer. Soc. of Hematology 71(3):539-555 (1988).
Kirby et al., "Role of Neural Crest in Congenital Heart Disease", Ciruclation 82(2):332-340 (1990).
Kirby et al., "Neural Crest and Cardiovascular Patterning", Cir. Res. 77(2):211-215 (1995).
Kohler et al., "Coninuous Cultures of Fused Cells Secreting Antibody of Predefiend Specificity", Nature 256:495-497 (1975).
Kolodkin et al., "Neuropilin is a Semaphorin III Receptor", Cell 90:753-762 (1997).
Kozak, "Regulation of Translation in Euraryotic Systems", Ann. Rev. Cell Biol. 8:197-225 (1992).
Larocca et al., "A Mr 46,000 Human Milk Fat Globule Protein That Is Highly Expressed in Human Breast Tumor Contains Factor VIII-Like Domains", Cancer Research 51:4994-98 (1991).
Lee et al., "The type I Iodothyronine 5'-Deiodinase Messenger Ribonuleic Acid Is Localized to the S3 Segment of the Rat Kidney Proximal Tubule", Endocrinology 132(5):2136-2140 (1993).
Lee et al., "The High Affinity Na/Glucose Cotransporter", J. Biol. Chem. 269(16):12032-12039 (1994).

(Continued)

Primary Examiner—David Romeo
(74) Attorney, Agent, or Firm—Mintz,Levin,Cohn,Ferris,Clovsky and Popeo, P.C.; Ingrid A. Beattie

(57) ABSTRACT

The invention features a aortic carboxypeptidase-like polypeptide (ACLP), DNA encoding ACLP, and methods of detecting genetic alterations associated with abdominal wall defects.

5 Claims, 3 Drawing Sheets

OTHER PUBLICATIONS

Li et al., "Vascular Smooth Muscle Cells Grown on Matrigel", J. Biol. Chem. 269(30):19653-19658 (1994).

Meinkoth et al., "Hybridization of nucleic acids immobilized on solid supports", Anal Biochem, 138(2):267-284 (1984).

Myers et al., "Detection of Single Base Substitutions by Ribonuclease Cleavage at Mismatches in RNA:DNA Duplexes" Science 230: 1242-1246 (1985).

Myers et al., "Detection and Localization of Single Base Changes by Denaturing Gradient Gel Electrophoresis", Methods in Enzymology 155:501-527 (1987).

Natsuaki et al., "Human skin mast cell carboxypeptidase: functional characterization, cDNA clongin, and geqnealogy", Journal of Investigative Dermatology, 99 (2):138-145 (1992).

New England Biolabs, Catalog #1014, p. 109 (1995).

Noden, "Embryonic Origins and Assembly of Blood Vessels", Amer. Rev. of Respiratory Dis. 140:1097-1103 (1989).

Ohno et al., "A cDNA Cloning of Human AEBP1 from Primary Cultured Osteoblasts and Its Expression in Differentiating Osteoblastic Cell Line", Biochem. Biophys. Res. Comm. 288:411-414 (1996).

Orita et al., "Detection of Polymorphisms of Human DNA by Gel Electrophoresis as Single-strand Conformation Polymorphisms", PNAS USA, 86:2766-2770 (1989).

Owens, "Regulation of Differentiation of Vascular Smooth Muscle Cells", Physiologigical Reviews 75:487-517 (1995).

Owens, "Expression of Smooth Muscle-specific α-Isoactin in Culured Vascular Smooth Cells: Relationship Between Growth and Cytodifferentiation", J. Cell Biol. 102:343-352 (1986).

Pierschbacher et al., "The Cell Attachment Determminant in Fibronectin", J. Cell. Biochem. 28:115-126 (1985).

Roberts et al., "Localization of E2A mRNA Expression in Developing and Adult Rat Tissues", PNAS USA 90:7583-7887 (1983).

Ross, "The Pathogenesis of Atherosclerosis: a Perspective for the 1990s", Nature 362:801-809 (1993).

Sambrook et al., "Molecular Cloning: A Laboratory Manual", Second Edition vols. 1, 2 and 3. Cold Spring Harbor Laboratory Press: Cols Spring Harbor, New York, U.S.A., pp. 9.50, 10.13 11.4, 16.2 and 17.2 (1989).

Sheffield et al., "Attachment of a 40-base-pair G+C Rich Sequence (GC-clamp) to Genomic DNA Fragments by the Polymerase Chain Reaction Results in Improved Detection . . . " PNAS USA 86:232-236 (1989).

Shrivastava et al., "An Orphan Receptor Tyrosine Kinase Family Whose Members Serve as Nonintegrin Collagen Receptors", Molecular Cell, 1:25-34 (1997).

Song et al., "Cloning and Expression of Human Carboxypeptidase Z, a Novel Metallocarboxy Peptidase", J. Biol. Chem. 272:10543-10550 (1997).

Springer et al., "Discoidin I Is Implicated in Cell-Substratum Attachement and Ordered Cell Mirgration of Dictyostelium Discoideum and Resembles Fibronectin", Cell 39:557-564 (1984).

Stemple et al., "Isolation of a Stem Cell for Neurons and Glia from the Mammalian Neural Crest", Cell 71:973-985 (1992).

Stubbs et al., "cDNA Cloning of a Mouse Mammary Epithelial Cell Surface Protein Reveals the Existence of Epidermal Growth Factor-Like Domains Linked to Factor VIII-like Sequences", PNAS USA 87:8417-8421 (1990).

Takagi et al., The A5 Antigen, a Candidate for the Neuronal Recognition Molecule, Has Homologies to Complement Components and Coagulation Factors, Neuron 7:295-307 (1991).

Tan et al., "Induction of Heparin-Binding Epidermal Growth Factor-Like Growth Factor mRNA by Protein Kinase C Activators", Kindney Int. 46:690-695 (1994).

Toole et al., "Molecular Cloning of a cDNA Encoding Human Antihaemophilic Factor", Nature 312:342-347 (1984).

Topouzis et al., "Smooth Muscle Lineage Divseristy in the Chick Embryo", Dev. Biol. 178:430-445 (1996).

Tracy et al., "Prothyrombinase Complex Assembly on the Platelet Surface is Mediated Through the 74,000-dalton Component of Factor Va", PNAS USA 80:2380-2384 (1983).

Vogel et al., "The Discooidin Domain Receptor Tyrosine Kinases Are Activated by Collagen", Molecular Cell 1:13-23 (1997).

von Heijne, "Signal Sequences", J. Mol. Biol., 184:99-105 (1985).

White et al., "Detecting Single Base Substitutions as Heteroduplex Polymorphisms", Genomics 12:301-306 (1992).

Yoshizumi et al., "Tumor Necrosis Factor Increases Transcription of the Heparin-binding Epidermal Growth factor-like Growth Factor Gene in Vascular Endothelial Cells", J. Biol. Chem. 267:9467-9469 (1992).

Yoshizumi et al., "Disappearance of Cyclin A Correlates with Permanent Withdrawal of Cardiomyocytes from the Cell Cycle in Human and Rat Hearts", J. Clin. Invest. 95:2275-2280 (1995).

Fig. 1A

AORTIC CARBOXYPEPTIDASE-LIKE POLYPEPTIDE

CROSS REFERENCE TO RELATED APPLICATIONS

This application is a divisional of application U.S. Ser. No. 09/060,482, filed on Apr. 16, 1998, which issued as U.S. Pat. No. 6,468,766, which is a continuation-in-part of U.S. Ser. No. 08/818,009 ABN, filed on Mar. 14, 1997, which in turn claims priority to provisional application U.S. Ser. No. 60/013,439, filed on Mar. 15, 1996, all of which are hereby incorporated by reference.

STATEMENT AS TO FEDERALLY SPONSORED RESEARCH

This invention was funded in part by the U.S. Government under grant numbers GM53249 awarded by the National Institutes of Health. The Government has certain rights in the invention.

BACKGROUND OF THE INVENTION

The invention relates to gastrointestinal abnormalities.

Gastroschisis is a life-threatening abdominal wall defect that occurs in approximately 1–7 of every 10,000 human births. The defect is thought to originate on the right side of the umbilical cord and may involve the formation of the omphalomesenteric artery. Infants with gastroschisis can be born with abdominal organs outside the body cavity, i.e., protruding through the defect. Factors associated with an increased risk for gastroschisis include a maternal age below 20 years, ingestion of aspirin, and ingestion of pseudoephedrine. The cause of gastroschisis has not been identified.

SUMMARY OF THE INVENTION

A novel human gene encoding aortic carboxypeptidase-like polypeptide (ACLP) has been discovered. A mutation in an ACLP gene has now been shown to be associated with the development of gastroschisis. Thus, a mutation in an ACLP gene is indicative of gastroschisis or a predisposition to develop the condition. Accordingly, the invention provides an isolated nucleic acid (e.g., genomic DNA, cDNA, or synthetic DNA) encoding an ACLP. By the term "human ACLP" is meant a polypeptide having the amino acid sequence of a naturally-occurring human ACLP. For example, the invention encompasses an ACLP with the amino acid sequence of SEQ ID NO:2 as well as naturally-occurring variants thereof such as mutant forms associated with gastroschisis or isoforms resulting from alternative splicing of exons of the ACLP gene.

The invention includes a nucleic acid molecule which contains the nucleotide sequence of human ACLP cDNA (SEQ ID NO:1). A nucleic acid molecule which contains nucleotides 140–3613 (ACLP coding sequence), inclusive, of SEQ ID NO:1 or a degenerate variant thereof, is also within the invention. Nucleotides 214–3613 encode an ACLP which lacks the first 25 residues (a putative signal peptide). Preferably, the nucleic acid molecule contains a nucleotide sequence encoding a polypeptide having an amino acid sequence that is at least 87% identical to the sequence of SEQ ID NO:2. More preferably, the sequence is at least 90% identical to SEQ ID NO:2, more preferably at least 95%, more preferably at least 98%, more preferably at least 99%, and most preferably, the nucleotide sequence encodes a polypeptide the amino acid sequence of which is SEQ ID NO:2.

An isolated nucleic acid molecule containing a strand which hybridizes at high stringency to a DNA having the sequence of SEQ ID NO:1, or the complement thereof is also within the invention. The nucleic acid molecule may be a primer useful to amplify ACLP DNA in a polymerase chain reaction (PCR). For example, the nucleic acid is at least 5 nucleotides but less than 50 nucleotides in length. Alternatively, the nucleic acid molecule may encompass the entire coding sequence of ACLP cDNA, i.e., nucleotides 140–3613, inclusive, of SEQ ID NO:1. Preferably, the nucleic acid molecule spans a gastroschisis-associated mutation in an ACLP gene. Such a molecule is useful as a hybridization probe to identify a genetic alteration, e.g., a deletion, duplication, point mutation, or translocation, that indicates that an individual has gastroschisis, is predisposed to developing gastroschisis, or is a heterozygous carrier of a genetic alteration associated with gastroschisis.

By "isolated nucleic acid molecule" is meant a nucleic acid molecule that is free of the genes which, in the naturally-occurring genome of the organism, flank an ACLP gene. The term therefore includes, for example, a recombinant DNA which is incorporated into a vector; into an autonomously replicating plasmid or virus; or into the genomic DNA of a procaryote or eucaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. The term excludes large segments of genomic DNA, e.g., such as those present in cosmid clones, which contain an ACLP gene flanked by one or more other genes which naturally flank it in a naturally-occurring genome.

Nucleic acid molecules include both RNA and DNA, including cDNA, genomic DNA, and synthetic (e.g., chemically synthesized) DNA. Where single-stranded, the nucleic acid molecule may be a sense strand or an antisense strand. The term therefore includes, for example, a recombinant DNA which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence.

Hybridization is carried out using standard techniques such as those described in Ausubel et al., *Current Protocols in Molecular Biology*, John Wiley & Sons, (1989). "High stringency" refers to DNA hybridization and wash conditions characterized by high temperature and low salt concentration, e.g., hybridization and wash conditions of 65° C. at a salt concentration of 0.1× SSC. "Low" to "moderate" stringency refers to DNA hybridization and wash conditions characterized by low temperature and high salt concentration, e.g. wash conditions of less than 60° C. at a salt concentration of at least 1.0× SSC. For example, high stringency conditions may include hybridization at 42° C. in a solution containing 50% formamide; a first wash at 65° C. using a solution of 2× SSC and 1% SDS; followed by a second wash at 65° C. using a solution of 0.1%× SSC. Lower stringency conditions suitable for detecting DNA sequences having about 50% sequence identity to an ACLP gene are detected by, for example, hybridization at 42° C. in the absence of formamide; a first wash at 2° C. in a solution of 6× SSC and 1% SDS; and a second wash at 50° C. in a solution of 6× SSC and 1% SDS.

TABLE 1

Human ACLP cDNA (SEQ ID NO:1)

```
   1 tccctcgctc accccatcct ctctcccgcc ccttcctgga ttccctcacc cgtctcgatc
  61 ccctctccgc cctttcccag agacccagag ccctgaccc cccgcgccct ccccggagcc
 121 ccccgcgcgt gccgcggcca tggcggccgt gcgcggggcg ccctgctca gctgcctcct
 181 ggcgttgctg gccctgtgcc ctggagggcg cccgcagacg gtgctgaccg acgacgagat
 241 cgaggagttc ctcgagggct tcctgtcaga gctagaacct gagccccggg aggacgacgt
 301 ggaggccccg ccgcctcccg agcccacccc gcgggtccga aaagcccagg cggggggcaa
 361 gccagggaag cggccaggga cggccgcaga agtgcctccg gaaaagacca agacaaagg
 421 gaagaaaggc aagaaagaca aaggccccaa ggtgcccaag gagtccttgg aggggtcccc
 481 caggccgccc aagaagggga aggagaagcc acccaaggcc accaagaagc caaggagaa
 541 gccacctaag gccaccaaga agcccaagga ggagccaccc aaggccacca agaagcccaa
 601 agagaagcca cccaaggcca ccaagaagcc cccgtcaggg aagaggcccc ccattctggc
 661 tccctcagaa accctggagt ggccactgcc cccaccccc agccctggcc ccgaggagct
 721 accccaggag ggaggggcgc ccctctcaaa taactggcag aatccaggag aggagaccca
 781 tgtggaggca caggagcacc agcctgagcc ggaggaggag accgagcaac ccacactgga
 841 ctacaatgac cagatcgaga gggaggacta tgaggacttt gagtacattc ggcgccagaa
 901 gcaacccagg ccaccccaa gcagaaggag gaggcccgag cgggtctggc cagagccccc
 961 tgaggagaag gccccggccc cagcccccgga ggagaggatt gagcctcctg tgaagcctct
1021 gctgcccccg ctgcccctg actatggtga tggttacgtg atccccaact acgatgacat
1081 ggactattac tttgggcctc ctccgcccca gaagcccgat gctgagcgcc agacggacga
1141 agagaaggag gagctgaaga aacccaaaaa ggaggacagc agccccaagg aggagaccga
1201 caagtgggca gtggagaagg gcaaggacca caaagagccc cgaaagggcg aggagttgga
1261 ggaggagtgg acgcctacgg agaaagtcaa gtgtccccc attgggatgg agtcacaccg
1321 tattgaggac aaccagatcc gagcctcctc catgctgcgc cacggcctgg gggcacagcg
1381 cggccggctc aacatgcaga ccggtgccac tgaggacgac tactatgatg gtgcgtggtg
1441 tgccgaggac gatgccagga cccagtggat agaggtggac accaggagga ctacccggtt
1501 cacaggcgtc atcacccagg gcagagactc cagcatccat gacgattttg tgaccacctt
1561 cttcgtgggc ttcagcaatg acagccagac atgggtgatg tacaccaacg gctatgagga
1621 aatgaccttt catgggaacg tggacaagga cacacccgtg ctgagtgagc tcccagagcc
1681 ggtggtggct cgtttcatcc gcatctaccc actcacctgg aatggcagcc tgtgcatgcg
1741 cctggaggtg ctggggtgct ctgtggcccc tgtctacagc tactacgcac agaatgaggt
1801 ggtggccacc gatgacctgg atttccggca ccacagctac aaggacatgc gccagctcat
1861 gaaggtggtg aacgaggagt gccccaccat cacccgcact acagcctggg caagagctc
1921 acgaggcctc aagatctatg ccatggagat ctcagacaac cctggggagc atgaactggg
1981 ggagcccgag ttccgctaca ctgctgggat ccatgcaac gaggtgctgg gccgagagct
2041 gttgctgctg ctcatgcagt acctgtgccc agagtaccgc gatgggaacc cacgtgtgcg
2101 cagcctggtg caggacacac gcatccacct ggtgccctca ctgaaccctg atggctacga
```

TABLE 1-continued

Human ACLP cDNA

```
2161 ggtggcagcg cagatgggct cagagtttgg gaactgggcg ctgggactgt ggactgagga
2221 gggctttgac atctttgaag atttcccgga tctcaactct gtgctctggg gagctgagga
2281 gaggaaatgg gtccctacc gggtccccaa caataacttg cccatccctg aacgctacct
2341 ttcgccagat gccacggtat ccacggaggt ccgggccatc attgcctgga tggagaagaa
2401 ccccttcgtg ctgggagcaa atctgaacg cggcgagcgg ctagtatcct accctacga
2461 tatgggcgc acgcctaccc aggagcagct gctggccgca gccatggcag cagcccgggg
2521 ggaggatgag gacgaggtct ccgaggccca ggagactcca gaccacgcca tcttccggtg
2581 gcttgccatc tccttcgcct ccgcacacct caccttgacc gagccctacc gcggaggctg
2641 ccaagcccag gactacaccg gcggcatggg catcgtcaac ggggccaagt ggaaccccg
2701 gaccgggact atcaatgact tcagttacct gcataccaac tgcctggagc tctccttcta
2761 cctgggctgt gacaagttcc ctcatgagag tgagctgccc cgcgagtggg agaacaacaa
2821 ggaggcgctg ctcaccttca tggagcaggt gcaccgcggc attaaggggg tggtgacgga
2881 cgagcaaggc atccccattg ccaacgccac catctctgtg agtggcatta atcacggcgt
2941 gaagacagcc agtggtggtg attactggcg aatcttgaac ccgggtgagt accgcgtgac
3001 agcccacgcg gagggctaca ccccgagcgc caagacctgc aatgttgact atgacatcgg
3061 ggccactcag tgcaacttca tcctggctcg ctccaactgg aagcgcatcc gggagatcat
3121 ggccatgaac gggaaccggc ctatcccaca catagaccca tcgcgcccta tgaccccca
3181 acagcgacgc ctgcagcagc gacgcctaca acaccgcctg cggcttcggg cacagatgcg
3241 gctgcggcgc ctcaacgcca ccaccaccct aggcccccac actgtgcctc ccacgctgcc
3301 ccctgccct gccaccaccc tgagcactac catagagccc tggggcctca taccgccaac
3361 caccgctggc tgggaggagt cggagactga gacctacaca gaggtggtga cagagtttgg
3421 gaccgaggtg gagcccgagt ttgggaccaa ggtggagccc gagtttgaga cccagttgga
3481 gcctgagttc gagacccagc tggaacccga gtttgaggaa gaggaggagg aggagaaaga
3541 ggaggagata gccactggcc aggcattccc cttcacaaca gtagagacct acacagtgaa
3601 ctttggggac ttctgagatc agcgtcctac caagaccca gcccaactca agctacagca
3661 gcagcacttc ccaagcctgc tgaccacagt cacatcaccc atcagcacat ggaaggcccc
3721 tggtatggac actgaaagga agggctggtc ctgccccttt gaggggtgc aaacatgact
3782 gggacctaag agccagaggc tgtgtagagg ctcctgctcc acctgccagt ctcgtaagag
3841 atgggggttgc tgcagtgttg gagtaggggc agagggaggg agccaaggtc actccaataa
3901 aacaagctca tggcaaaaaa aaaaaaaaa aaaaa
```

The invention also includes a substantially pure human ACLP polypeptide. A substantially pure ACLP polypeptide may be obtained, for example, by extraction from a natural source (e.g., a vascular smooth muscle cell); by expression of a recombinant nucleic acid encoding an ACLP; or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight, ACLP. A substantially pure ACLP may be obtained, for example, by extraction from a natural source (e.g., a vascular smooth muscle cell); by expression of a recombinant nucleic acid encoding an ACLP; or by chemically synthesizing the protein. Purity can be measured by any appropriate method, e.g., column chromatography, polyacrylamide gel electrophoresis, or HPLC analysis. Accordingly, substantially pure polypeptides include recombinant polypeptides derived from a eucaryote but produced in E. coli or another procaryote, or in a eucaryote other than that from which the polypeptide was originally derived.

For expression of recombinant ACLP, an ACLP-encoding nucleic acidc is operably linked to a regulatory sequence, e.g., a promoter. By "promoter" is meant a minimal DNA sequence sufficient to direct transcription. Promoters may be constitutive or inducible, and may be coupled to other regulatory sequences or "elements" which render promoter-dependent gene expression cell-type specific, tissue-specific or inducible by external signals or agents; such elements may be located in the 5' or 3' region of the native gene, or within an intron. DNA encoding an ACLP may be operably linked to such regulatory sequences for expression of the polypeptide in procaryotic or eucaryotic cells. By "operably linked" is meant that a coding sequence and a regulatory sequence(s) are connected in such a way as to permit gene expression when the appropriate molecules (e.g., transcriptional activator proteins) are bound to the regulatory sequence(s).

To produce recombinant ACLP, a cell containing an ACLP-encoding sequence operably linked to appropriate regulatory sequences is cultured under conditions permitting expression of a nucleic acid molecule. The cell may be a procaryotic cell or a eucaryotic cell. To obtain post-translationally modified, e.g., glycosylated recombinant ACLP, the recombinant polypeptide is produced in a eucaryotic cell, e.g., a yeast or mammalian cell.

An ACLP preferably contains an amino acid sequence that is at least 87% identical to the amino acid sequence of SEQ ID NO:2. More preferably, the amino acid sequence is at least 90% (more preferably at least 95%, more preferably at least 98%, more preferably at least 99%) identical to SEQ ID NO:2. Most preferably, the polypeptide contains the amino acid sequence of SEQ ID NO:2.

The invention also includes polypeptides which contain a portion of naturally-occurring ACLP, e.g., an ACLP fragment containing a lysine-rich/proline rich domain (amino acids 117–164 of SEQ ID NO:2), an ACLP fragment containing a discoidin-like domain (amino acids 385–540 of SEQ ID NO:2), or an ACLP fragment containing a carboxypeptidase-like domain (amino acids 562–969 of SEQ ID NO:2).

Where a particular polypeptide or nucleic acid molecule is said to have a specific percent identity to a reference polypeptide or nucleic acid molecule of a defined length, the percent identity is relative to the reference peptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 10 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 25 nucleotides, preferably at least 50 nucleotides, more preferably at least 75 nucleotides, and most preferably 100 nucleotides or 300 nucleotides.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

TABLE 2

Human ACLP amino acid sequence (SEQ ID NO:2)
MAAVRGAPLLSCLLALLALCPGGRPQTVLTDDEIEEFLEGFLSELEPEPR

EDDVEAPPPPEPTPRVRKAQAGGKPGKRPGTAAEVPPEKTKDKGKKGKKD

KGPKVPKESLEGSPRPPKKGKEKPPKATKKPKEKPPKATKKPKEEPPKAT

KKPKEKPPKATKKPPSGKRPPILAPSETLEWPLPPPPSPGPEELPQEGGA

PLSNNWQNPGEETHVEAQEHQPEPEEETEQPTLDYNDQIEREDYEDFEYI

RRQKQPRPPPSRRRRPERVWPEPPEEKAPAPAPEERIEPPVKPLLPPLPP

DYGDGYVIPNYDDMDYYFGPPPPQKPDAERQTDEEKEELKKPKKEDSSPK

EETDKWAVEKGKDHKEPRKGEELEEEWTPTEKVKCPPIGMESHRIEDNQI

RASSMLRHGLGAQRGRLNMQTGATEDDYYDGAWCAEDDARTQWIEVDTRR

TTRFTGVITQGRDSSIHDDFVTTFFVGFSNDSQTWVMYTNGYEEMTFHGN

VDKDTPVLSELPEPVVARFIRIYPLTWNGSLCMRLEVLGCSVAPVYSYYA

QNEVVATDDLDFRHHSYKDMRQLMKVVNEECPTITRTYSLGKSSRGLKIY

AMEISDNPGEHELGEPEFRYTAGIHGNEVLGRELLLLLMQYLCREYRDGN

PRVRSLVQDTRIHLVPSLNPDGYEVAAQMGSEFGNWALGLWTEEGFDIFE

DFPDLNSVLWGAEERKWVPYRVPNNNLPIPERYLSPDATVSTEVRAIIAW

MEKNPFVLGANLNGGERLVSYPYDMARTPTQEQLLAAAMAAARGEDEDEV

SEAQETPDHAIFRWLAISFASAHLTLTEPYRGGCQAQDYTGGMGIVNGAK

WNPRTGTINDFSYLHTNCLELSFYLGCDKFPHESELPREWENNKEALLTF

MEQVHRGIKGVVTDEQGIPIANATISVSGINHGVKTASGGDYWRILNPGE

YRVTAHAEGYTPSAKTCNVDYDIGATQCNFILARSNWKRIREIMAMNGNR

PIPHIDPSRPMTPQQRRLQQRRLQHRLRLRAQMRLRRLNATTTLGPHTVP

PTLPPAPATTLSTTIEPWGLIPPTTAGWEESETETYTEVVTEFGTEVEPE

FGTKVEPEFETQLEPEFETQLEPEFEEEEEEEKEEEIATGQAFPFTTVET

YTVNFGDF

A substantially pure DNA containing an ACLP promoter/enhancer sequence (SEQ ID NO:3) is useful for directing transcription of DNA encoding all or part of ACLP or of DNA encoding a heterologous polypeptide (e.g., a polypeptide other than ACLP or an ACLP the sequence of which corresponds to a naturally-occurring ACLP of a species other than the species from which the promoter/enhancer sequence is derived). For example, a murine ACLP promoter/enhancer sequence may be operably linked to DNA encoding human ACLP for therapeutic expression of ACLP in human patients. To regulate transcription of the polypeptide-encoding sequence (e.g., developmental stage-specific transcription), the promoter/enhancer sequence is operably linked to a polypeptide-encoding sequence. The ACLP promoter/enhancer sequence directs transcription of a polypeptide-encoding sequence.

By "promoter/enhancer sequence" is meant a DNA sequence located 5' to the transcriptional start site of the ACLP gene and which contains one or more cis-acting elements which regulate transcription, e.g., cell specific transcription. The elements may be contiguous or separated by DNA not involved in the regulation of transcription, e.g., an enhancer element may be in a position immediately adjacent to the promoter element or up to several kilobases upstream or downstream of the transcriptional start site. The promoter/enhancer DNA is preferably derived from the 5' region of a mammalian ACLP gene, such as that of the mouse (SEQ ID NO:3), and regulates expression of a polypeptide-encoding DNA to which it is operably linked. The promoter/enhancer sequence regulates developmental stage-specific expression, e.g., expression in embryonic cells, of a polypeptide-encoding sequence.

TABLE 3

Mouse ACLP promoter/enhancer (SEQ ID NO:3)
AAGCTTAGTCTCCCTCTCTCCTGGCTCCTCTCCTGGGGCTTCCCTATGGA

GGTAGCACTTACAGAAGATGCTTGTTCCAAACCTTCAGGGGTACAAACTA

CACAGATATACTGAAGGACAGGAGGCTGGGGCCTCCCCCCACCCCCAACA

GCCACTGTTCTCTCAGGAGCTCTGCTTCTGCTCTGCAGCATTGAAAACAA

AACTGAAGGACACCTTCCTTCTCTCAGGCCAGCCCAGTGCTGTTGTGTGA

TCCCTCGGGAAGACTCTAACGCATTCACAGGGACAACAGGAGTTGGGAGG

GAGAGGAGTTACAGAACTTTCCAGCAGGACCTCAGGAGAACGCCTGGACA

CGGACAGGAACCCCCAACCCCTCAGGGACCCCCTTGGACCCTTTGAGTGC

TCCTGATCATGGAAGCCACCAGCCTCCCGATTCCTCAGCTGTGGCCTTGG

CAGTGCCCTCTGGACATTTGACTTAAACGCTATGCTCTTCAGCAGAGTGG

AGAGCTCTCCTCACAGGCTCTGGCTTCTGGTTGTCCTCTTGCCCCAGCGC

TGTGGGCCCAGGTTAGAAAGACTTCCTGAGGACAGGCTCCCTCAGGAGGA

TCCCCAGCGTACGACTGTGCTCCCACGCACCTTTCCGGATTTTCTGTGTG

GAGGCCTCAACCCCTCAGGCCTCCTGGGCCAGCTCCTCTGCTCGAATTCC

TGTCCGTGACTCATTGAGGCTCAGGAAAAGGCTTTCTAGACCTTAGGTTT

CTTTGTTTTCCATTTTTGAAATGGCTTCTGTTTTCCCTGGCAGAGAATAT

CCAACCCAAATTCAGTCCAAGTATGACCCATGCCTAGGGAAGTGACATCC

ATGTCCCCTCATGCACCCTGTGGCATACCCAGCATGACACACTGGACCAG

ACTGGGGGCACGGAAGCCAATTCCCAGAACTGACTTTGAGCACAATGATT

CAGAGGGTGACCATGAGTGAGACTTGCTTTACTCTTGCTCTGCGACCAGG

TTGAAGTCTCTCATGGGGAGGCCTAGCTGTGAGAGGATTGTCCTGGGATG

GGGGAAGGGGGAGCAAAGTGGATGAGGACCAACAGCCTGTGGGATGCAAG

GGCTGATCGTGTGTGCTAGGCACAGCACAAAGTGGTCCATTTAGCCGGGC

AGTGGTGGTGCACACCTTTAATCCCAGCACTTGGGAGGCATCAGCAGGTG

GGTTTCTGAGTTCGAGGCCAGCCTGGTCTACAGAGCAAGTTCCAGGACAG

CCAGAGCTACACAGAGAAACTCTGTCTCAAAAAAATCGAATAAACCAGAA

TABLE 3-continued

Mouse ACLP promoter/enhancer

AGGTGGTCCATTTAATATGCGTATAGTAAGTTGTGGACACGGGAGTTCCC

CTGCTGAGTCAGACAGCTAGGAGGGCTAAGATGGGTTAGACCCTCCCCCC

CCCCACACACACACACACACACTCACACACACATCAGTTCTTGGCATAGT

CTCCATGCTTCCTCAAGGAGAGCCAGAAAGGAGACTGCCGGGAGGAGCTT

GCCTACTCCCTGAGAGCAGTGGGTTACAGAGCCCAGTGCCCGAAAATTTC

CCCTTTTTCTCCCTGCTCATGCTGGACAGAGAGGGTGAGGGTGAGGGTGA

AAGACTGAGGAGGTGGCATCGTGTTGGTGTTTCTTGACCTGCTTTTTCTT

TTTTCTCTTCCAGCTGAGATGTAAACTTTCCCATGTCAATCATCTGGGGG

TCGCTATTCTTTTTTATCAGAGTGCCTCCCCACCTTGGTTGAAAGCTGCC

TGCCACTACCCTGGACCTATGGCTGCTACAAGCCCACGTTCACATCTTTA

ATCCTTCATGGGTAAATGCTCTGGCATTCCTGGGCTTAGCTATGATGGCC

ATTATGAGCCAGCCAACGTTTGTATTCTAGAAGCCATAGCTGAAGCTGTT

GTAAACAATTTGTTGTTTTAACCGCTTCTGGTCAGAGGAAGGAGAGAATA

GCTATTACTCCACATTGGGACCTGAGCCCTGAGCTCTGAAGTGGGGCTCC

TATCTCCATAAGGACAGCAGCTTGCTGAGAACAGCTTTTCACAGCCTTCC

TCGCAAAAATTGGCTCCAAAGACCTGGGATGTTGGTGATAACTGGACAAA

GGTGACACCTGTGCAAGCACACAGCAGGTGACACTTTGAAGAGCTAACCT

CCAGAAAGTGGAAAGGAGGTGATCGCCAGTACCCTCGAGGGCCCTACTCC

CTCCCTCCCCTAGCAATCTCCCTGGGCTCAGAGCAAAGGGCACAGCGGGT

TAGAGCACAGGTCTCCTTAGACTCCCCACACTCCCTTCCCCATAACTGTT

GCATTCTTTTCTCCCAGGCCTTCCTCCCCGCTAGGCGCCCTGCACCCACA

CCCTCTAAACTGGCGCGTGACGCTGCTATTAGTCTGGGCTCCGTGCTGTC

CGCCTCCCTCCCCCGCAGCCCCGGTCCAAGGCCGGCTCCTCCTCCTCCC

CCTCCGGAAACCCGAAGCCCCCGCCCCGGCCAGGCCGTCGCAAGCGCTCT

GGAGGGCGGTCCGCGTGAGAGCCAGCCACGCGGGGCAGGAGCGCCCAGTT

GCTGCCGGAGCTGGGCCCGCCAGAACCTCTCCTGGAGCCCCTTGCTCTCC

TTGAATCTCCCTTTCCCACCGCTTTCTGGATACCCTTGACGCCCACGTTC

CTCGCGCCCTTTCCCGCCCCTACGCGGGGCGCTGCCCCTGCCACCCAAGT

CCCTGCTCAAGCCCGCCCGGTCCCGCGCGTGCCCAGAGCCATG

The invention also includes a vector containing the promoter/enhancer DNA of the invention (operably linked to a polypeptide-encoding DNA sequence), and a vascular smooth muscle cell containing the vector. Also within the invention is a method of directing vascular smooth cell-specific expression of the polypeptide by introducing the vector into a vascular smooth muscle cell and maintaining the cell under conditions which permit expression of the polypeptide, e.g., introducing the vector into a human patient for gene therapy.

A method of detecting a gastroschisis-associated genetic alteration is carried out by providing a sample of DNA or RNA from a patient or fetus, and determining whether the DNA or RNA contains a mutation in a gene encoding an ACLP. Detection of such an ACLP mutation indicates that the patient or fetus has a genetic alteration that is associated with the development of gastroschisis. The presence of a gastroschisis-associated genetic alteration is diagnostic of gastroschisis or a predisposition to developing gastroschisis. The method can also be used to identify heterozygous carriers of a mutation associated with gastroschisis. Such individuals may be asymptomatic but are at risk of having children which are homozygous for an ACLP mutation (and therefore, likely to develop clinical gastroschisis). Tissue samples from adult patients are obtained by conventional means, e.g., biopsy or venipuncture. Prenatal testing is carried out by obtaining fetal tissue samples, e.g., by amniocentesis or chorionic villi sampling.

Patient-derived DNA is examined for genetic abnormalities in the ACLP gene, e.g., by detecting restriction fragment length polymorphisms (RFLPs), deletions, point mutations, or other defects. The diagnostic method includes the step of subjecting the sample to polymerase chain reaction (PCR), using a forward PCR primer complementary to a portion of the antisense strand of the gene, the portion being within (a) a first intron of the gene, or (b) the 5' untranslated region adjacent to the start codon of the gene; and a reverse PCR primer complementary to a fragment of the sense strand of the gene, this fragment being within (a) a second intron of the gene, or (b) the 3' untranslated region adjacent to the termination codon of the gene. PCR can also be used to detect mutations in an ACLP promoter or other regulatory sequences using primers that flank the mutation. ACLP mutations and/or aberrant ACLP expression can also be detected using standard hybridization techniques, such as Northern blotting.

Fragments of ACLP are useful to raise ACLP-specific antibodies. Accordingly, the invention includes an antibody, e.g., a polyclonal antisera or a monoclonal antibody preparation, that selectively binds to an ACLP. ACLP-specific antibodies are used to diagnose gastroschisis or a predisposition thereto. For example, a diagnostic method is carried out by providing a tissue sample from a patient or fetus, and detecting expression of an ACLP gene in the tissue sample. Expression is measured by detecting the amount of ACLP-specific antibody that binds to the tissue sample, e.g., by ELISA assay, Western blot assay, or immunohistochemical staining of tissue sections. Expression of ACLP is also measured by detecting the level of ACLP transcript in the tissue sample. Regardless of the method of detection of ACLP expression, a reduction in the amount of expression in the patient-derived tissue sample compared to the level of expression in a normal control tissue sample indicates that the patient or fetus from which the sample was obtained has or is predisposed to developing gastroschisis.

Methods of treating or preventing the development of gastroschisis are also within the invention. For example, one treatment regimen includes the steps of identifying a patient with or at risk of developing gastroschisis, and introducing into cells of the patient an isolated nucleic acid encoding ACLP, e.g., a nucleic acid which contains the nucleotide sequence of 140 to 3613 of SEQ ID NO:1. The cells into which the DNA was introduced produce the recombinant ACLP to compensate for a gastroschisis-associated genetic alteration, e.g., a mutation resulting in reduced production of ACLP or a mutation resulting in the production of a defective ACLP. Rather than administering ACLP-encoding DNA to the patient, an ACLP (e.g., a polypeptide having the sequence of SEQ ID NO:2) or a fragment thereof may be introduced into the patient.

An animal model for gastroschisis is useful to study the development of the condition as well as to evaluate therapeutic approaches to treatment or prevention of gastroschisis. A genetically-altered non-human mammal, all diploid cells of which contain a mutation in an endogenous gene encoding an ACLP, is included in the invention. For example, a mammal with a homozygous null mutation in its ACLP gene(s) develops gastroschisis. Preferably, the mammal is a rodent such as a mouse. The genetically altered non-human mammal produces altered levels of ACLP or mutant forms of ACLP. The levels of ACLP gene product in the genetically altered mammal can be increased or decreased at different time periods during development. By "genetically altered mammal" is meant a mammal in which the genomic DNA sequence has been manipulated in some way. The genetically altered mammal may be a knockout in which the endogenous ACLP sequences have been deleted or otherwise altered to decrease or change the pattern of expression. Alternatively, the genetically altered mammal may be transgenic. For example, the transgenic mammal may express ACLP sequences from another species, may overexpress ACLP gene product, or may express ACLP in tissues and at developmental stages other than those in which ACLP is expressed in a wild type animal.

The nucleated cells of a genetically altered mammal not producing a functional endogenous ACLP may be engineered to encode a human ACLP, and to express functional human ACLP, or, alternatively, ACLP from another heterologous species.

Preferably, the genetically altered non-human mammal is a rodent such as a mouse or a rat, the germ cells and somatic cells of which contain a mutation in DNA encoding ACLP. All diploid cells of such an animal contain a mutation in one or both alleles of the endogenous ACLP gene. The mutation can, for example, be a deletion, an insertion, or a nucleotide substitution. The mutation could be in the ACLP regulatory regions or in the coding sequence. It can, e.g., introduce a stop codon that results in production of a truncated, inactive gene product or it can be a deletion of all or a substantial portion of the coding sequence. For example, one or more exons, e.g., exons 7–15, of an ACLP gene may be deleted. By the term "null mutation" is meant a mutation that reduces the expression or activity level of the protein encoded by the mutated gene by more than 80% relative to the unmutated gene. A mouse harboring such a null mutation is a knockout mouse. An ACLP knockout mouse, i.e., one that harbors a homozygous ACLP null mutation, has been found to have an abdominal defect with an extrusion of abdominal organs i.e., gastroschisis.

The invention also includes a mammalian cell line, e.g., immortalized ACLP deficient cells, the genomic DNA of which contains a null mutation in DNA encoding ACLP. Such cells lack the ability to synthesize full length functional ACLP. The cells harboring the null mutation may be derived from a cell obtained from a ACLP deficient mammal, e.g., an ACLP knockout mouse.

Compounds capable of promoting expression or function of an ACLP may be therapeutically useful to treat gastroschisis. Accordingly, the invention includes a method of screening a candidate compound to identify a compound capable of stimulating expression of an ACLP, e.g., human ACLP, by (a) providing a cell or tissue expressing capable of expressing a ACLP, (b) contacting the cell or tissue with the candidate compound, and (c) determining the amount of expression of the ACLP by the cell. An increase in the amount of ACLP expression in the presence of the candidate compound compared to that in the absence of the candidate compound indicates that the compound stimulates expression of the ACLP.

In addition to diagnostic methods, such as described above, the present invention encompasses methods and compositions for evaluating appropriate treatment, and treatment effectiveness of pathological conditions associated with aberrant expression of ACLP. For example, the ACLP gene can be used as a probe to classify cells in terms of their level of ACLP expression, or as a source of primers for diagnostic PCR analysis in which mutations and allelic variation of ACLP can be detected.

Other features and advantages of the invention will be apparent from the following description of the preferred embodiments thereof, and from the claims.

BRIEF DESCRIPTION OF THE DRAWING

Figure 1A:
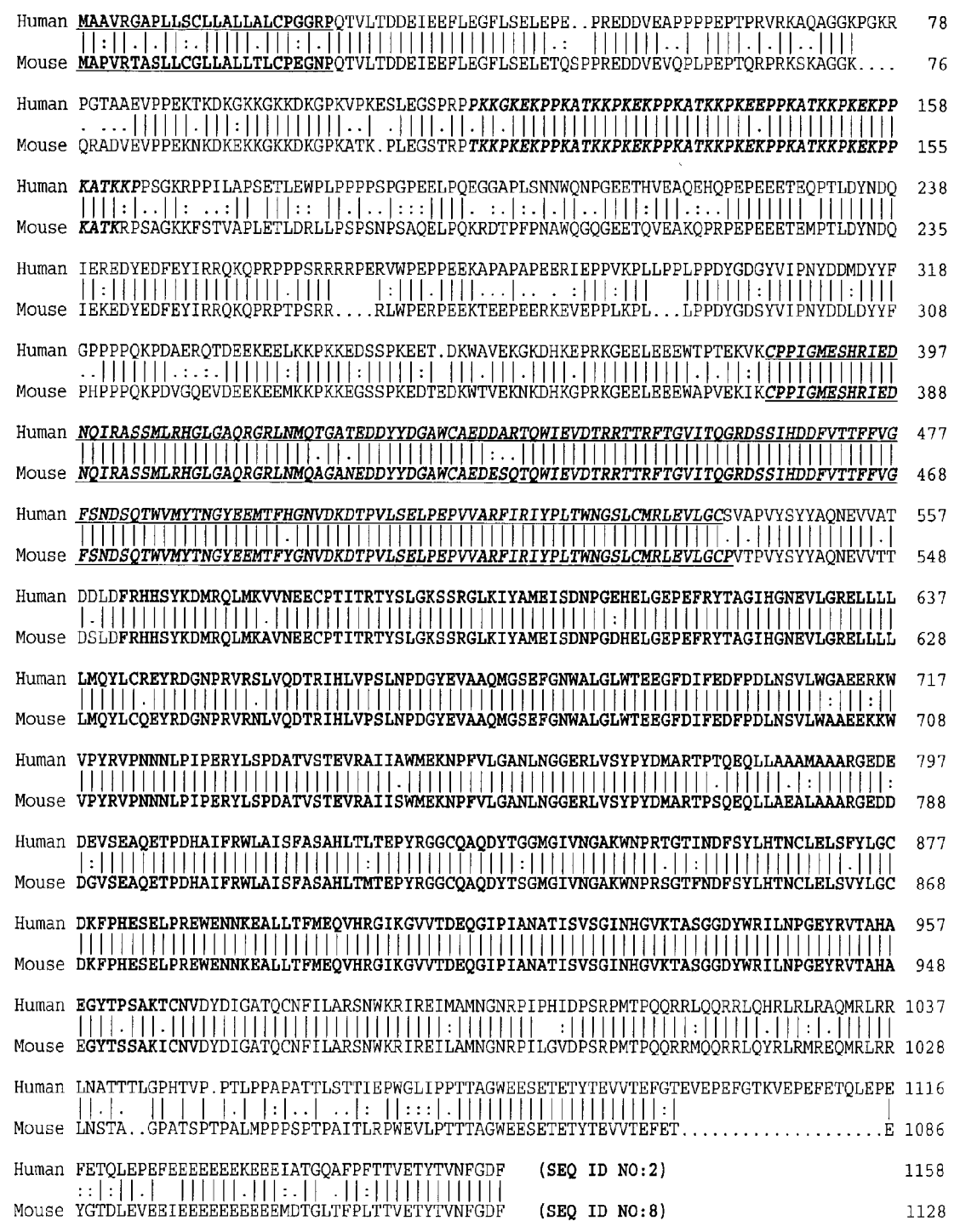

FIG. 1A is a diagram showing a comparison of deduced open reading frames of human ACLP and mouse ACLP. The human and mouse proteins contain 1158 and 1128 amino acids, respectively. Highlighted motifs include a signal peptide (bold, underline), a 4-fold lysine- and proline-rich repeating motif (bold, italic), a discoidin-like domain (bold, italic, underline), and a region with homology to the carboxypeptidases (bold).

DETAILED DESCRIPTION

Figure 1B:
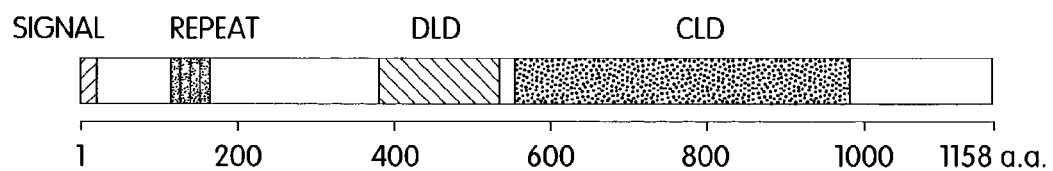
FIG. 1B is a diagram showing the location of peptide domains of human ACLP. The signal peptide sequence at the N-terminus is designated "Signal"; the 4-fold repeating motif is designated "Repeat"; the discoidin-like domain is designated "DLD"; and the region with homology to carboxypeptidases is designated "CLD".

A mutation in an ACLP-encoding nucleic acid resulting in a decrease in production of an ACLP compared to the level of ACLP production in an animal lacking the mutation has now been shown to result in the development of gastroschisis in newborn mice. The following examples describe the cloning and characterization of human ACLP and methods of diagnosing and treating gastroschisis the underlying defect of which is a genetic alteration in the ACLP genes.

EXAMPLE 1

Cloning of ACLP Genes

ACLP was identified in a screen for proteins interacting with the E47 product of the E2A gene. A recombinant E47 fusion protein (N3-SH[ALA]), containing the basic helix loop helix domain of hamster shPan-1 (amino acids 509–646, with mutations R551A, V552L, and R553A) with a heart muscle kinase recognition sequence and the FLAG epitope, was expressed and purified as described (Blanar et al., 1995, Proc. Natl. Acad. Sci. USA 92:5870–4; Blanar and Rutter, 1992, Science 256:1014–8). N3-SH[ALA] was phosphorylated by heart muscle kinase in the presence of $\gamma$-$^{32}$P-ATP and used to screen a human aorta λgt11 cDNA expression library (Clonetech) by interaction cloning (Blanar et al., 1995, Proc. Natl. Acad. Sci. USA 92:5870–4; Blanar and Rutter, 1992, Science 256:1014–8). A 1450-bp cDNA clone (ΔE2A-BP) obtained from interaction cloning was radiolabeled by random priming and used to isolate a 2786 bp cDNA clone from the same human aorta λgt11 cDNA library. Data from Northern blotting experiments revealed that the ACLP-1 RNA was about 3.9 kb in size and suggested that the 2786 bp cDNA clone was a partial cDNA clone. Additional 5' sequences of the ACLP cDNA were isolated by 5' rapid amplification of cDNA ends from human aortic smooth muscle cell RNA (Gibco-BRL). The full length sequence of the human ACLP cDNA was found to be 3935 bp and is shown in Table 1 (SEQ ID NO:1). The full length human ACLP cDNA contains an open reading frame (nucleotides 140–3613 of SEQ ID NO:1) encoding a polypeptide of 1158 amino acids. The open reading frame is preceded by a Kozak consensus translation initiation sequence, which in turn is preceded by an in frame stop codon.

The human ACLP protein has a calculated molecular mass of 130 kDa, an estimated pI of 4.8, and contains a putative signal peptide sequence. In addition, it contains an 11 amino acid lysine- and proline-rich motif repeated four times at the N-terminus, a domain with 30% amino acid identity to the slime mold adhesion protein discoidin I, and a C-terminal domain with 39% identity to carboxypeptidase E. The human ACLP gene maps to the short arm of chromosome 7 (between D7S478 amd D7S519).

The sequence of the human ACLP cDNA (GENBANK™ accession number AF053944) was compared to sequences present in GENBANK™ databases. A 3' portion of ACLP cDNA was found to share homology with the sequence of a cDNA encoding mouse adipocyte enhancer binding protein 1 (AEBP1; He et al., 1995, Nature 378:92). AEBP1 was originally identified as a 2.5 kb cDNA that hybridized to a 4 kb band on Northern blot analysis, and was predicted to encode a 719 amino acid, 79 kDa protein.

To isolate mouse ACLP cDNA (GENBANK™ accession number AF053943), first strand cDNA from C2C12 mouse myoblast total RNA was synthesized by reverse transcription with the primer 5' ATCTGGTTGTCCTCAAT 3' (SEQ ID NO:4). The nested primer 5' TGACTCCATCCCAATAG 3' (SEQ ID NO:5) and the anchor primer included in the kit for 5' rapid amplification of cDNA ends was then amplified to produce a product of approximately 1400 bp in size. This product was sequenced using standard methods.

The entire open reading frame of mouse ACLP was then amplified from C2C12 RNA by reverse transcription PCR (EXPANDLONG™ Template PCR System, Boehringer Mannheim, Indianapolis, Ind.). The human and mouse clones were sequenced by the dideoxy nucleotide chain termination method using a combination of Sequenase Version 2.0 (Amersham, Arlington Heights, Ill.), the Thermo Sequenase $^{33}$P terminator cycle sequencing kit (Amersham), and the Thermo Sequenase fluorescent-labeled cycle sequencing kit with 7-deaza-GTP (Amersham) on a Licor (Lincoln, Nebr.) apparatus.

Sequencing of the 3633 bp mouse ACLP cDNA fragment, revealed that it encoded an open reading frame (1128 amino acids) similar to that of the full-length human ACLP cDNA, indicating that it is the mouse ACLP homologue. A comparison of the human and mouse ACLP amino acid sequences is shown in FIG. 1A. Overall, the two proteins are 85% identical and 90% similar.

EXAMPLE 2

Figure 2A:
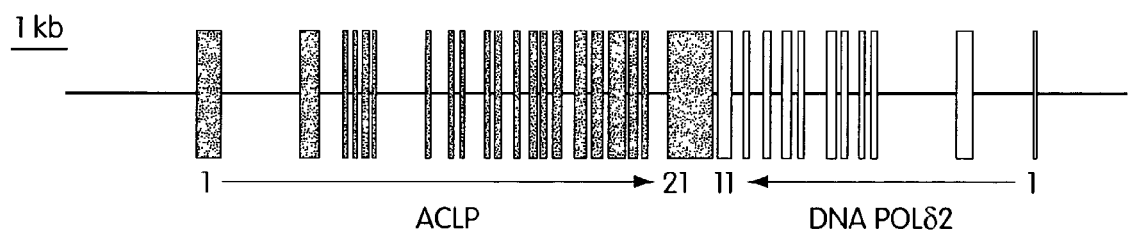
FIG. 2A is a diagram of mouse genomic DNA showing a map of the mouse ACLP gene and neighboring DNA polymerase delta small subunit gene.
Figure 2B:
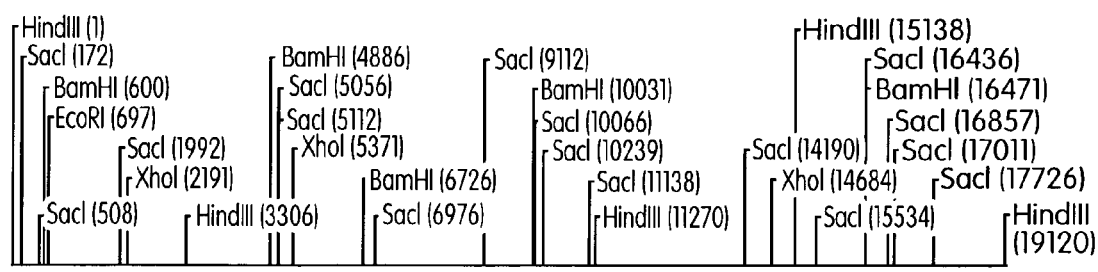
FIG. 2B is a diagram of a restriction map of genomic DNA containing the mouse ACLP gene and neighboring DNA polymerase delta small subunit gene.

Identification of a Promoter-Enhancer Sequence Associated with the ACLP Gene To identify genomic sequences that mediate tissue specific and developmental expression pattern of the ACLP gene, a region of genomic DNA adjoining the 5' end of the mouse ACLP coding sequences was isolated (FIGS. 2A and 2B). Portions of this genomic DNA were then used in reporter transfection assays to determine their ability to direct expression of a reporter gene in transfection assays. ACLP promoter/enhancer DNA was cloned into the pGL2 Basic vector (Stratagene) and transfected into rat aortic smooth muscle cells (RASMC) to measure promoter activity. Using this assay, a region containing an ACLP promoter/enhancer sequence was identified and is shown in Table 3 (SEQ ID NO:3). ACLP promoter/enhancer DNA was found to have transcriptional activity both in vitro (using cultured cells) and in vivo (in a transgenic mouse).

EXAMPLE 3

Generation and Characterization of Antibodies to ACLP Peptides

A carboxy terminal fragment of mouse ACLP was expressed in bacteria, purified, and used as an immunogen to raise antibodies in rabbits.

To produce a polyclonal anti-ACLP antibody, a BamHI-EcoRI fragment of mouse ACLP (encoding amino acids 615–1128) was subcloned into the pRSET C bacterial expression vector (Invitrogen), and the resulting plasmid was transformed into BL21(DE3)pLysS-competent bacteria (Stratagene). Protein expression was induced with 1 mM isopropyl β-D-thiogalactopyranoside for 3 h. Bacteria were sonicated in lysis buffer (50 mM $NaH_2PO_4$, 10 mM Tris, pH 8, 100 mM NaCl) containing the protease inhibitors aprotinin, leupeptin, and phenylmethylsulfonyl fluoride. Lysates were clarified by centrifugation at 10,000 g for 15 min, and the pellet was resuspended in lysis buffer supplemented with 8 M urea. His-tagged proteins were purified with Talon resin (Clontech) and eluted in lysis buffer containing 8 M urea and 100 mM ethylene diamine tetraacetic acid. Proteins were dialyzed against water and measured with the Bio-Rad (Hercules, Calif.) protein assay reagent. 100 μg of the purified protein was used to immunize New Zealand white rabbits. Antiserum was collected, titered against the recombinant protein, and used for immunoblot analysis. Specificity of the antiserum was determined by using preimmune serum and by competition with a recombinant protein. The same methods are used to raise antibodies to human ACLP. The rabbit antisera raised against a portion of mouse ACLP was found to crossreact with human ACLP.

Protein extracts from cultured cells were prepared for Western blotting in extraction buffer (25 mM Tris, pH 7.4, 50 mM NaCl, 0.5% sodium deoxycholate, 2% Nonidet P-40, and 0.2% sodium dodecyl sulfate) containing the protease inhibitors aprotinin, leupeptin, and phenylmethylsulfonyl fluoride. To obtain proteins from mouse tissues, individual organs were homogenized in 25 mM Tris, pH 7.5, 50 mM NaCl, and 10 mM ethylene diamine tetraacetic acid containing protease inhibitors (Complete, Boehringer Mannheim). Proteins were measured with the BCA protein assay kit (Pierce, Rockford, Ill.). After 50 μg aliquots had been resolved on 6% sodium dodecyl sulfate-polyacrylamide gels (18), proteins were transferred electrophoretically to nitrocellulose membranes (Schleicher and Schuell, Keene, N.H.) in 48 mM Tris, pH 8.3, 39 mM glycine, 0.037% sodium dodecyl sulfate, and 20% methanol transfer buffer. Blots were equilibrated with 25 mM Tris, pH 8, 125 mM NaCl, and 0.1% Tween 20 and blocked in the same solution containing 4% nonfat dry milk. Blots were incubated with anti-ACLP serum diluted 1:1000 and then horseradish peroxidase-conjugated goat anti-rabbit serum diluted 1:4000. Membranes were processed with an enhanced chemiluminescence reagent (ECL reagent, NEN, Boston, Mass.) and exposed to film.

By Western blot analysis, this antibody detected a single band corresponding to a protein with an apparent mobility of approximately 175 kDa in mouse aortic smooth muscle cells (MASMC) extracts. This protein showed a similar migration to a protein generated by transcription and translation in vitro of a mouse ACLP cDNA clone, providing additional evidence that the isolated human and mouse cDNA clones encode full-length ACLP.

Monoclonal antibodies can be obtained using full-length human or mouse ACLP or fragments thereof using standard methods, e.g., the process described by Milstein and Kohler, 1975, Nature 256:495–97, or as modified by Gerhard, 1980, Monoclonal Antibodies, Plenum Press, pages 370–371. Hybridomas are screened to identify those producing antibodies that are specific for an ACLP. Preferably, the antibody will have an affinity of at least about $10^8$ liters/mole and more preferably, an affinity of at least about $10^9$ liters/mole.

EXAMPLE 4

Subcellular Localization and Tissue Localization of ACLP Proteins

To assess the subcellular localization of ACLP, a mouse ACLP expression construct was generated with a c-myc epitope at the C-terminus. The myc epitope was placed at the C-terminus to avoid interference with signal peptide-mediated processes, e.g., ACLP secretion mechanisms. To construct a c-myc-tagged ACLP expression plasmid (pcDNA3.1/ACLP-Myc-His), the open reading frame of mouse ACLP was amplified with the Expand Long Template PCR System (Boehringer Mannheim). A 5' primer containing an EcoRI site (5' CGGAATTCAGTCCCTGCT-CAAGCCCG 3'; SEQ ID NO:6) and a 3' primer containing a HindIII site (5' CGAAGCTTGAAGTCCCCAAAGT-TCACTG 3'; SEQ ID NO:7) was used, which resulted in the deletion of the endogenous termination codon in the PCR product. The PCR product was then digested with EcoRI and HindIII restriction enzymes and ligated into the EcoRI and HindIII sites of pcDNA3.1(−)/Myc-His A (Invitrogen). Cells were transfected transiently with pcDNA3.1/ACLP-Myc-His by the DEAE-dextran method with minor modifications (Tan et al., Kidney International 46:690, 1994). Twenty-four hours after transfection, cells were trypsinized and plated onto chamber slides (Nunc, Naperville, Ill.) and grown for an additional 24 h. Cells were fixed with 4% paraformaldehyde in phosphate-buffered saline and immunostained using standard methods. Amonoclonal anti-c-myc primary antibody (9E10 Ab-1, Oncogene Research Products, Cambridge, Mass.) and a rhodamine-conjugated goat anti-mouse IgG secondary antibody were used to immunostain the cells. Nuclei were counterstained with Hoechst 33258 (1 μg/ml) and visualized with a fluorescence microscope.

RASMC and A7r5 cells both exhibited strong membrane-associated or cytoplasmic staining. Staining was most intense in the perinuclear region and was not observed in the nucleus. Various other tissues were examined for the presence of ACLP mRNA and protein. Gene expression studies confirmed expression in aortic smooth muscle cells, and levels of ACLP mRNA were found to be high in the whole aorta (including adventitia) compared to most other tissue types tested, e.g., heart, brain, stomach, thymus, and liver. ACLP message was also detectable in colon and kidney tissue.

To examine expression of ACLP, extracts from mouse tissues were subjected to Western blot analysis using anti-ACLP sera. ACLP was strongly expressed in the mouse aorta (without adventitia) but not in the adventitia, heart, liver, skeletal muscle, or kidney. The presence of ACLP mRNA in the kidney (but absence of protein) indicates that the level of ACLP in the cells is regulated at the level of translation of ACLP mRNA into polypeptide.

To identify cell types expressing ACLP in an adult animal, in situ hybridization was performed on adult rat aorta and skeletal muscle using known methods. Adult male Sprague-Dawley rats were perfused with 4% paraformaldehyde and their organs were removed and sectioned. ACLP mRNA was detected with a [$^{35}$S]UTP-labeled antisense riboprobe synthesized with SP6 RNA polymerase from a linearized 0.7 kb fragment of ACLP cDNA. As a control, a sense RNA probe was synthesized with T7 RNA polymerase from a linearized ACLP cDNA fragment. The antisense riboprobe detected specific ACLP expression in the smooth muscle cells of the aorta, whereas the control (sense) probe did not. Neither the sense nor the antisense probe hybridized to skeletal muscle cells.

EXAMPLE 5

ACLP Expression in Smooth Muscle Cell Differentiation

ACLP protein expression was examined during vascular smooth muscle cell growth and differentiation. RASMC and MASMC were isolated from the thoracic aortas of adult male Sprague-Dawley rats and C57Bl/6 mice using standard methods. Human aortic smooth muscle cells (HASMC) were purchased from Clonetics (San Diego, Calif.), and rat A7r5 smooth muscle cells and C2C12 mouse myoblasts were purchased from the American Type Culture Collection (Rockville, Md.). Mouse neural crest cells (Monc-1 cells) were cultured on fibronectin-coated plates. RASMC, MASMC, and A7r5 cells were cultured in Dulbecco's modified Eagle's medium with 3.7 g/liter glucose (Gibco-BRL, Gaithersburg, Md.) supplemented with 10% fetal bovine serum (Hyclone, Logan, Utah), 4 mML-glutamine, 100 μg/ml streptomycin, 100 units/ml penicillin, and 10 mM HEPES (pH 7.4). C2C12 cells were grown in Dulbecco's modified Eagle's medium supplemented with 15% fetal bovine serum, 4 mM L-glutamine, 100 μg/ml streptomycin, and 100 units/ml penicillin. HASMC were cultured in M199 medium (Gibco) supplemented with 20% fetal bovine serum, 4 mM L-glutamine, 100 μg/ml streptomycin, and 100 units/ml penicillin. Cells were grown at 37° C. in a humidified incubator containing 5% $CO_2$. MASMC were cultured for 3 days in 0.4% calf serum containing medium that induces quiescence. RNA and protein extracts were then prepared from the cells and analyzed.

The amount of ACLP mRNA was higher (about 2-fold) in serum-starved (quiescent) MASMC than in control cells (normal proliferating MASMC). In RASMC, ACLP mRNA was approximately 3-fold more abundant in quiescent cells than in their actively proliferating counterparts. ACLP protein was also elevated in quiescent MASMC.

ACLP expression was examined in an in vitro system for differentiating smooth muscle cells from a Monc-1 cell line, a mouse line derived from the neural crest. Monc-1 cells differentiate into smooth muscle cells when tissue culture medium supplemented with chick embryo extract is replaced with differentiation medium. To examine ACLP expression during the transition of undifferentiated Monc-1 cells to smooth muscle, the time course of ACLP expression was measured. ACLP mRNA was nearly undetectable in undifferentiated Monc-1 cells. As the cells differentiated, however, ACLP expression increased until it became marked at days 4 and 6 after the start of differentiation. Under these conditions, induction of ACLP appeared to lag behind that of smooth muscle a-actin, a marker for smooth muscle cells. To compare the level of ACLP protein in cells treated similarly, protein extracts were prepared from undifferentiated Monc-1 cells and from cells allowed to differentiate for 6 days. ACLP protein was not detectable in undifferentiated Monc-1 cells but was expressed highly (day 6) under conditions that promote Monc-1 cell differentiation into smooth muscle cells. The abundance of ACLP protein in these cells was similar to that in MASMC.

As is described below, the Monc-1 cells (and other cells expressing ACLP) can be used to screen for compounds that stimulate a therapeutic increase in ACLP production (e.g., during cell differentiation and/or fetal development).

EXAMPLE 6

Genetically-Altered Animals

An ACLP deficient animal, e.g., an ACLP knockout mouse, is produced as follows.

Figure 3:
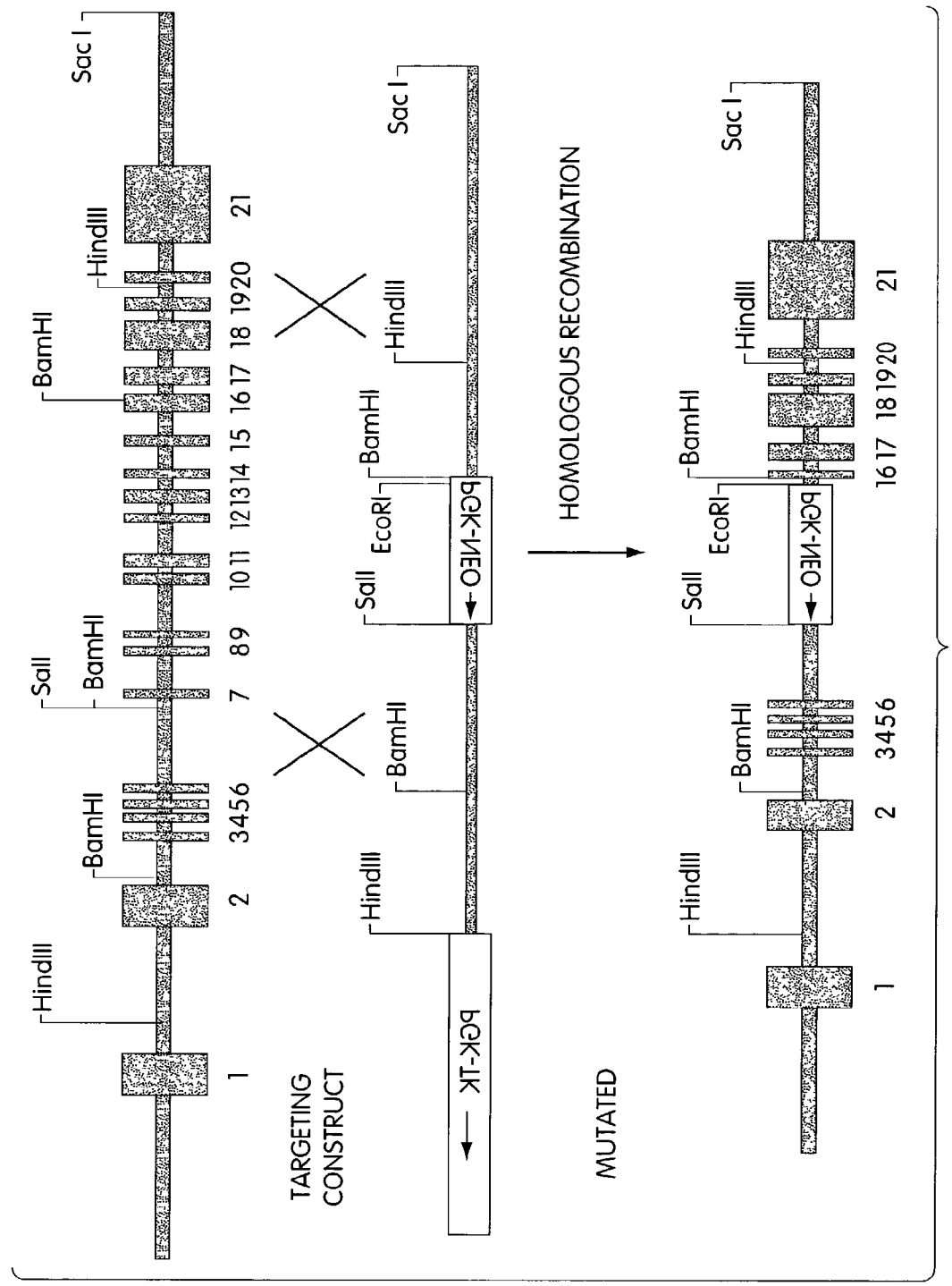
FIG. 3 is a diagram showing a map of the targeting construct used to make an ACLP knockout mouse.

The targeting construct was made by deleting exons, e.g., 7–15 of the mouse ACLP gene (see FIG. 3). A SalI-BamHI fragment of the ACLP gene was replaced with pPGK-neo to generate the targeting construct.

The linearized targeting construct (shown in FIG. 3) was transfected into murine D3 embryonic stem (ES) cells, and a clone with the correct homologous recombination (yielding the appropriately disrupted ACLP gene shown in FIG. 3) injected into blastocysts and used to generate ACLP chimeric mice using standard methods. The chimeric mice were bred with wild type mice to generate ACLP-mutated heterozyous mice. ACLP-mutated heterozygous mice were born normal. To generate an ACLP knockout mouse (i.e., homozygous for the ACLP mutation), the heterozygous mice were mated. The genotype of newborn mice was evaluated at 3 weeks. Out of 205 live pups, 74 were found to have the wild type ACLP gene, 113 were found to be heterozygotes, and 18 were found to be homozygous for the ACLP null mutation, i.e., ACLP knockout mice. These data indicate that many of the knockout mice died before or immediately after birth.

The phenotype of ACLP knockout mice was evaluated during development. Cesarean sections were performed to obtain embryos at 18.5 embryonic days (El8.5). ACLP-knockout mice were found to have an abdominal defect with extrusion of abdominal organs, whereas the wild type mice were normal.

The progress of the development of gastroschisis is evaluated by mating heterozygous ACLP-mutant mice and obtaining embryos at various time points, e.g., E18.5, E16.5, E12.5, E10.5, and E8.5. Embryos are examined at both gross and microscopic levels. Histological evaluation of embryonic tissue, e.g., to follow the formation of the omphalomesenteric arteries, is used to determine the incidence and time of development of gastroschisis.

ACLP-deficient animals can be used to screen for compounds to treat or prevent the development of gastroschisis. To determine whether a given compound prevents or reduces the development of gastroschisis in developing embryos, the compound is administered to the pregnant animal (e.g., systemically, in utero, or directly to an embryo itself) and the embryos examined as described above. For example, a nucleic acid encoding a full length wild type ACLP gene (or an ACLP gene which may differ from the wild type sequence but still retains ACLP function) can be tested to evaluate the effect of such gene therapy on the development of gastroschisis. A reduction in the severity of gastroschisis in treated embryos compared to untreated embryos indicates that the compound or gene therapy approach to treatment of gastroschisis is clinically beneficial.

ACLP deficient mice and ACLP deficient cell lines derived from such mice are useful in determining the etiology of gastroschisis and screening for therapeutic compositions.

EXAMPLE 7

Diagnosis of Disorders Associated with Altered Levels of ACLP Expression or Activity The data described herein indicates that an ACLP mutation (e.g., in ACLP coding or regulatory sequences) is involved in the development of gastroschisis. Thus, individuals (e.g., those with a family history of the disease) can be tested for the presence of a mutated ACLP gene which may contribute to the development of gastroschisis in children of an individual harboring a mutated gene. Detection of such a mutation will permit appropriate genetic counseling of those individuals regarding the risks associated with pregnancy. In addition, such testing can be used to identify individuals with subclinical gastroschisis or other related gastrointestinal abnormalities. Prenatal testing may be carried out to determine whether a developing fetus is at risk of developing gastroschisis. Although gastroschisis may be detected at approximately the second trimester of pregnancy by conventional prenatal ultrasound testing, early detection of a genetic abnormality permits early intervention, including genetic therapy, which may prevent the development of the condition or reduce its severity.

Analysis can be carried out on any suitable genomic DNA sample (e.g., maternal tissue and/or fetal tissue) to be tested. Typically, a blood sample or a sample of placental or umbilical cord cells is tested. A sample of fetal cells can be obtained by amniocentesis or chorionic villi sampling.

Standard genetic diagnostic methods are used to detect a mutation in the ACLP gene. For example, PCR (polymerase chain reaction) is used to identify the presence of a deletion, addition, or substitution of one or more nucleotides within any one of the exons of ACLP. Following the PCR reaction, the PCR product can be analyzed by methods as described above, such as the heteroduplex detection technique based upon that of White et al., 1992, Genomics 12:301–306, or by techniques such as cleavage of RNA-DNA hybrids using RNase A (Myers et al., 1985, Science 230:1242–1246); single-stranded conformation polymorphism (SSCP) analysis (Orita et al., 1989, Genomics 10:298–299); and denaturing gradient gel electrophoresis (DGGE; Myers et al., 1987, Methods Enzymol. 155:501–527). PCR may be carried out using a primer which adds a G+C-rich sequence (termed a "GC-clamp") to one end of the PCR product, thus improving the sensitivity of the subsequent DGGE procedure (Sheffield et al., 1989, Proc. Natl. Acad. Sci. USA 86:232–236). If the particular mutation present in the patient's family is known to have removed or added a restriction site, or to have significantly increased or decreased the length of a particular restriction fragment, a protocol based upon restriction fragment length polymorphism (RFLP) analysis (perhaps combined with PCR) can be used to identify the genetic defect.

In addition to evaluating genomic DNA of a patient, an ACLP defect can be detected by evaluating an ACLP gene product. Unlike genomic DNA-based diagnostic methods, this approach permits detection of defects resulting in a decrease in the level of expression of an ACLP gene (i.e., a defect which does not involve mutations in the coding sequence itself). In addition to detection of a gene product, gene expression is also measured using mRNA-based methods, such as Northern blots and in situ hybridization (using a nucleic acid probe derived from the relevant cDNA), and quantitative PCR.

An ACLP gene product can be tested for abnormalities, e.g., differences in the level of expression compared to wild type ACLP, truncation of an ACLP gene product, or deletion of a portion of an ACLP gene product. Deletion ACLP mutants, e.g., those characterized by the loss of an ACLP epitope, can be detected using an ACLP-specific antibody. Western blotting and Northern blotting techniques are used to quantitate the amount of expression of a ACLP in the tissue of interest. For example, an individual who is heterozygous for a genetic defect affecting level of expression of ACLP may be diagnosed by detecting reduction in the level of expression of this gene in such a hybridization or antibody-based assay, and an individual who is homozygous may be identified by detection of a comparatively lower level of expression.

The diagnostic method of the invention is carried out by measuring ACLP gene expression in a tissue, e.g, a biopsy, or in a bodily fluid, e.g., blood or plasma. Detection of expression and determination of the level of gene expression is measured using methods known in the art, e.g., in situ hybridization, Northern blot analysis, or Western blot analysis using ACLP-specific monoclonal or polyclonal antibodies. An decrease in the level of ACLP expression per cell in the test sample of tissue compared to the level per cell in control tissue indicates that the patient has gastroschisis, is predisposed to developing gastroschisis, or is a carrier of a genetic defect associated with gastroschisis.

The diagnostic procedures described above are useful to identify patients in need of therapeutic intervention to reduce the severity of or prevent the development of gastroschisis.

EXAMPLE 8

Treatment of Disorders Associated with Altered Levels of ACLP Expression or Activity Gene therapy may be carried out by administering to a patient a nucleic acid encoding a therapeutic polypeptide, e.g., an ACLP or fragment thereof, by standard vectors and/or gene delivery systems. Suitable gene delivery systems may include liposomes, receptor-mediated delivery systems, naked DNA, and viral vectors such as herpes viruses, retroviruses, adenoviruses and adeno-associated viruses, among others.

In addition to a gene delivery system as described above, the therapeutic composition may include a pharmaceutically acceptable carrier, e.g., a biologically compatible vehicle such as physiological saline, suitable for administration to an animal. A therapeutically effective amount of a compound is an amount which is capable of producing a medically desirable result in a treated animal, e.g., a reduction in the severity of gastroschisis or the prevention of the development of gastroschisis (e.g., in a fetus).

Parenteral administration, such as intravenous, subcutaneous, intramuscular, and intraperitoneal delivery routes, may be used to deliver the compound. Dosage for any one patient depends upon many factors, including the patient's size, body surface area, age, the particular compound to be administered, sex, time and route of administration, general health, and other drugs being administered concurrently. Dosage of the compound to be administered will vary. A preferred dosage for intravenous administration of nucleic acids is from approximately $10^6$ to $10^{22}$ copies of the nucleic acid molecule. Compounds, including therapeutic nucleic acids, may be administered locally through the uterine wall to the developing fetus using known methods.

ACLPs may be similarly administered, e.g., locally or systemically, e.g., intravenously, in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 μmoles of the polypeptide of the invention would be administered per kg of body weight per day. The compositions of the invention are useful for parenteral administration, such as intravenous, subcutaneous, intramuscular, and intraperitoneal.

ACLP encoding DNA is be introduced into target cells of the patient by standard vectors, e.g., a vector which contains DNA encoding an ACLP operably linked to an ACLP promoter/enhancer sequence. Suitable gene delivery systems may include liposomes, receptor-mediated delivery systems, naked DNA, and viral vectors such as herpes viruses, retroviruses, and adenoviruses, among others. ACLP DNA under the control of a strong constitutive promoter may be administered locally using an adenovirus delivery system.

Drugs which stimulate an-endogenous ACLP promoter may also be administered as described above to increase the level of expression ACLP in patients in which the underlying clinical defect is a pathologically low level of ACLP production.

EXAMPLE 9

Identification of Compounds that Alter ACLP Expression or Activity

ACLP knockout mice have the clinical manifestations of gastroschisis. Compositions that ameliorate the symptoms of gastroschisis or prevent the development of gastroschisis in a developing fetus can be identified using ACLP knockout mice. A test compound is administered to an ACLP knockout mouse. As a control, the compound is administered to a normal wild type mouse (preferably with the same genetic background as the ACLP knockout mouse). A reduction in the severity of gastroschisis in ACLP knockout mice treated with the test compound compared to control ACLP mice which have not been exposed to the test compound is an indication that the test compound is capable of ameliorating the symptoms of or preventing the development of gastroschisis.

Compounds can also be screened by contacting cells in vitro, e.g., VASMC, MASMC, RASMC, Monc-1 cells, or cells derived from an ACLP knockout mouse or from an animal or patient with gastroschisis, with a candidate compound and measuring the level of ACLP expression (or activity) in the cells. An increase in cellular ACLP expression (compared to the level of expression in the absence of a test compound) indicates that the compound is clinically useful to prevent or treat gastroschisis in which the underlying defect is pathological reduction in the level of ACLP production.

Other embodiments are within the following claims.

What is claimed is:

1. An isolated polypeptide comprising an amino acid sequence which is at least 87% identical to SEQ ID NO:2 over the entire length of SEQ ID NO: 2 and which amino acid sequence comprises
   (a) a discoidin domain comprising amino acids 385–540 of SEQ ID NO:2;
   (b) a lysine-rich/proline-rich domain comprising amino acids 117–164 of SEQ ID NO: 2; and
   (c) a carboxypeptidase domain comprising amino acids 562–969 of SEQ ID NO:2, wherein an amino acid substitution in said polypeptide is conservative with respect to SEQ ID NO:2 and wherein the absence of said polypeptide is associated with gastroschisis.

2. The isolated polypeptide of claim 1, wherein said amino acid sequence is at least 90% identical to the sequence of SEQ ID NO:2 over the entire length of SEQ ID NO:2.

3. The isolated polypeptide of claim 1, wherein said amino acid sequence is at least 95% identical to the sequence of SEQ ID NO:2 over the entire length of SEQ ID NO:2.

4. The isolated polypeptide of claim 1, wherein said amino acid sequence is at least 99% identical to the sequence of SEQ ID NO:2 over the entire length of SEQ ID NO:2.

5. An isolated polypeptide comprising the amino acid sequence of SEQ ID NO:2.

* * * * *

UNITED STATES PATENT AND TRADEMARK OFFICE
CERTIFICATE OF CORRECTION

| | | |
|---|---|---|
| PATENT NO. | : 7,094,878 B2 | Page 1 of 1 |
| APPLICATION NO. | : 10/238876 | |
| DATED | : August 22, 2006 | |
| INVENTOR(S) | : Lee et al. | |

It is certified that error appears in the above-identified patent and that said Letters Patent is hereby corrected as shown below:

In the Specification

Column 1, Line 18, cancel the text beginning with "This invention" and ending "numbers GM53249" in Line 19 and insert the following:
--This invention was made with government support under GM053249--

Signed and Sealed this
Nineteenth Day of August, 2025

Coke Morgan Stewart
*Acting Director of the United States Patent and Trademark Office*

SEQUENCE LISTING

```
<160> NUMBER OF SEQ ID NOS: 8

<210> SEQ ID NO 1
<211> LENGTH: 3935
<212> TYPE: DNA
<213> ORGANISM: Homo sapiens
<220> FEATURE:
<221> NAME/KEY: CDS
<222> LOCATION: (140)...(3613)

<400> SEQUENCE: 1
tccctcgctc accccatcct ctctcccgcc ccttcctgga ttccctcacc cgtctcgatc      60
ccctctccgc cctttcccag agacccagag cccctgaccc cccgcgccct ccccggagcc     120 cccgcgcgt gccgcggcc atg gcg gcc gtg cgc ggg gcg ccc ctg ctc agc      172
                    Met Ala Ala Val Arg Gly Ala Pro Leu Leu Ser
                     1               5                  10 tgc ctc ctg gcg ttg ctg gcc ctg tgc cct gga ggg cgc ccg cag acg      220
Cys Leu Leu Ala Leu Leu Ala Leu Cys Pro Gly Gly Arg Pro Gln Thr
         15                  20                  25 gtg ctg acc gac gac gag atc gag gag ttc ctc gag ggc ttc ctg tca      268
```

```
                                                                -continued

Val Leu Thr Asp Asp Glu Ile Glu Glu Phe Leu Glu Gly Phe Leu Ser
         30                  35                  40 gag cta gaa cct gag ccc cgg gag gac gac gtg gag gcc ccg ccg cct      316
Glu Leu Glu Pro Glu Pro Arg Glu Asp Asp Val Glu Ala Pro Pro Pro
         45                  50                  55 ccc gag ccc acc ccg cgg gtc cga aaa gcc cag gcg ggg ggc aag cca      364
Pro Glu Pro Thr Pro Arg Val Arg Lys Ala Gln Ala Gly Gly Lys Pro
 60                  65                  70                  75 ggg aag cgg cca ggg acg gcc gca gaa gtg cct ccg gaa aag acc aaa      412
Gly Lys Arg Pro Gly Thr Ala Ala Glu Val Pro Pro Glu Lys Thr Lys
                 80                  85                  90 gac aaa ggg aag aaa ggc aag aaa gac aaa ggc ccc aag gtg ccc aag      460
Asp Lys Gly Lys Lys Gly Lys Lys Asp Lys Gly Pro Lys Val Pro Lys
             95                 100                 105 gag tcc ttg gag ggg tcc ccc agg ccg ccc aag aag ggg aag gag aag      508
Glu Ser Leu Glu Gly Ser Pro Arg Pro Pro Lys Lys Gly Lys Glu Lys
         110                 115                 120 cca ccc aag gcc acc aag aag ccc aag gag aag cca cct aag gcc acc      556
Pro Pro Lys Ala Thr Lys Lys Pro Lys Glu Lys Pro Pro Lys Ala Thr
 125                 130                 135 aag aag ccc aag gag gag cca ccc aag gcc acc aag aag ccc aaa gag      604
Lys Lys Pro Lys Glu Glu Pro Pro Lys Ala Thr Lys Lys Pro Lys Glu
140                 145                 150                 155 aag cca ccc aag gcc acc aag aag ccc ccg tca ggg aag agg ccc ccc      652
Lys Pro Pro Lys Ala Thr Lys Lys Pro Pro Ser Gly Lys Arg Pro Pro
                 160                 165                 170 att ctg gct ccc tca gaa acc ctg gag tgg cca ctg ccc ccc ccc          700
Ile Leu Ala Pro Ser Glu Thr Leu Glu Trp Pro Leu Pro Pro Pro Pro
             175                 180                 185 agc cct ggc ccc gag gag cta ccc cag gag gga ggg gcg ccc ctc tca      748
Ser Pro Gly Pro Glu Glu Leu Pro Gln Glu Gly Gly Ala Pro Leu Ser
         190                 195                 200 aat aac tgg cag aat cca gga gag gag acc cat gtg gag gca cag gag      796
Asn Asn Trp Gln Asn Pro Gly Glu Glu Thr His Val Glu Ala Gln Glu
 205                 210                 215 cac cag cct gag ccg gag gag gag acc gag caa ccc aca ctg gac tac      844
His Gln Pro Glu Pro Glu Glu Glu Thr Glu Gln Pro Thr Leu Asp Tyr
220                 225                 230                 235 aat gac cag atc gag agg gag gac tat gag gac ttt gag tac att cgg      892
Asn Asp Gln Ile Glu Arg Glu Asp Tyr Glu Asp Phe Glu Tyr Ile Arg
                 240                 245                 250 cgc cag aag caa ccc agg cca ccc cca agc aga agg agg agg ccc gag      940
Arg Gln Lys Gln Pro Arg Pro Pro Pro Ser Arg Arg Arg Arg Pro Glu
             255                 260                 265 cgg gtc tgg cca gag ccc cct gag gag aag gcc ccg gcc cca gcc ccg      988
Arg Val Trp Pro Glu Pro Pro Glu Glu Lys Ala Pro Ala Pro Ala Pro
         270                 275                 280 gag gag agg att gag cct cct gtg aag cct ctg ctg ccc ccg ctg ccc     1036
Glu Glu Arg Ile Glu Pro Pro Val Lys Pro Leu Leu Pro Pro Leu Pro
 285                 290                 295 cct gac tat ggt gat ggt tac gtg atc ccc aac tac gat gac atg gac     1084
Pro Asp Tyr Gly Asp Gly Tyr Val Ile Pro Asn Tyr Asp Asp Met Asp
300                 305                 310                 315 tat tac ttt ggg cct cct ccg ccc cag aag ccc gat gct gag cgc cag     1132
Tyr Tyr Phe Gly Pro Pro Pro Pro Gln Lys Pro Asp Ala Glu Arg Gln
                 320                 325                 330 acg gac gaa gag aag gag gag ctg aag aaa ccc aaa aag gag gac agc     1180
Thr Asp Glu Glu Lys Glu Glu Leu Lys Lys Pro Lys Lys Glu Asp Ser
             335                 340                 345
```

```
                                                          -continued
agc ccc aag gag gag acc gac aag tgg gca gtg gag aag ggc aag gac     1228
Ser Pro Lys Glu Glu Thr Asp Lys Trp Ala Val Glu Lys Gly Lys Asp
    350                 355                 360 cac aaa gag ccc cga aag ggc gag gag ttg gag gag gag tgg acg cct     1276
His Lys Glu Pro Arg Lys Gly Glu Glu Leu Glu Glu Glu Trp Thr Pro
365                 370                 375 acg gag aaa gtc aag tgt ccc ccc att ggg atg gag tca cac cgt att     1324
Thr Glu Lys Val Lys Cys Pro Pro Ile Gly Met Glu Ser His Arg Ile
380                 385                 390                 395 gag gac aac cag atc cga gcc tcc tcc atg ctg cgc cac ggc ctg ggg     1372
Glu Asp Asn Gln Ile Arg Ala Ser Ser Met Leu Arg His Gly Leu Gly
                400                 405                 410 gca cag cgc ggc cgg ctc aac atg cag acc ggt gcc act gag gac gac     1420
Ala Gln Arg Gly Arg Leu Asn Met Gln Thr Gly Ala Thr Glu Asp Asp
            415                 420                 425 tac tat gat ggt gcg tgg tgt gcc gag gac gat gcc agg acc cag tgg     1468
Tyr Tyr Asp Gly Ala Trp Cys Ala Glu Asp Asp Ala Arg Thr Gln Trp
        430                 435                 440 ata gag gtg gac acc agg agg act acc cgg ttc aca ggc gtc atc acc     1516
Ile Glu Val Asp Thr Arg Arg Thr Thr Arg Phe Thr Gly Val Ile Thr
    445                 450                 455 cag ggc aga gac tcc agc atc cat gac gat ttt gtg acc acc ttc ttc     1564
Gln Gly Arg Asp Ser Ser Ile His Asp Asp Phe Val Thr Thr Phe Phe
460                 465                 470                 475 gtg ggc ttc agc aat gac agc cag aca tgg gtg atg tac acc aac ggc     1612
Val Gly Phe Ser Asn Asp Ser Gln Thr Trp Val Met Tyr Thr Asn Gly
                480                 485                 490 tat gag gaa atg acc ttt cat ggg aac gtg gac aag gac aca ccc gtg     1660
Tyr Glu Glu Met Thr Phe His Gly Asn Val Asp Lys Asp Thr Pro Val
            495                 500                 505 ctg agt gag ctc cca gag ccg gtg gtg gct cgt ttc atc cgc atc tac     1708
Leu Ser Glu Leu Pro Glu Pro Val Val Ala Arg Phe Ile Arg Ile Tyr
        510                 515                 520 cca ctc acc tgg aat ggc agc ctg tgc atg cgc ctg gag gtg ctg ggg     1756
Pro Leu Thr Trp Asn Gly Ser Leu Cys Met Arg Leu Glu Val Leu Gly
    525                 530                 535 tgc tct gtg gcc cct gtc tac agc tac tac gca cag aat gag gtg gtg     1804
Cys Ser Val Ala Pro Val Tyr Ser Tyr Tyr Ala Gln Asn Glu Val Val
540                 545                 550                 555 gcc acc gat gac ctg gat ttc cgg cac cac agc tac aag gac atg cgc     1852
Ala Thr Asp Asp Leu Asp Phe Arg His His Ser Tyr Lys Asp Met Arg
                560                 565                 570 cag ctc atg aag gtg gtg aac gag gag tgc ccc acc atc acc cgc act     1900
Gln Leu Met Lys Val Val Asn Glu Glu Cys Pro Thr Ile Thr Arg Thr
            575                 580                 585 tac agc ctg ggc aag agc tca cga ggc ctc aag atc tat gcc atg gag     1948
Tyr Ser Leu Gly Lys Ser Ser Arg Gly Leu Lys Ile Tyr Ala Met Glu
        590                 595                 600 atc tca gac aac cct ggg gag cat gaa ctg ggg gag ccc gag ttc cgc     1996
Ile Ser Asp Asn Pro Gly Glu His Glu Leu Gly Glu Pro Glu Phe Arg
    605                 610                 615 tac act gct ggg atc cat ggc aac gag gtg ctg ggc cga gag ctg ttg     2044
Tyr Thr Ala Gly Ile His Gly Asn Glu Val Leu Gly Arg Glu Leu Leu
620                 625                 630                 635 ctg ctg ctc atg cag tac ctg tgc cga gag tac cgc gat ggg aac cca     2092
Leu Leu Leu Met Gln Tyr Leu Cys Arg Glu Tyr Arg Asp Gly Asn Pro
                640                 645                 650 cgt gtg cgc agc ctg gtg cag gac aca cgc atc cac ctg gtg ccc tca     2140
Arg Val Arg Ser Leu Val Gln Asp Thr Arg Ile His Leu Val Pro Ser
            655                 660                 665
```

-continued

```
ctg aac cct gat ggc tac gag gtg gca gcg cag atg ggc tca gag ttt    2188
Leu Asn Pro Asp Gly Tyr Glu Val Ala Ala Gln Met Gly Ser Glu Phe
        670                 675                 680 ggg aac tgg gcg ctg gga ctg tgg act gag gag ggc ttt gac atc ttt    2236
Gly Asn Trp Ala Leu Gly Leu Trp Thr Glu Glu Gly Phe Asp Ile Phe
    685                 690                 695 gaa gat ttc ccg gat ctc aac tct gtg ctc tgg gga gct gag gag agg    2284
Glu Asp Phe Pro Asp Leu Asn Ser Val Leu Trp Gly Ala Glu Glu Arg
700                 705                 710                 715 aaa tgg gtc ccc tac cgg gtc ccc aac aat aac ttg ccc atc cct gaa    2332
Lys Trp Val Pro Tyr Arg Val Pro Asn Asn Asn Leu Pro Ile Pro Glu
                720                 725                 730 cgc tac ctt tcg cca gat gcc acg gta tcc acg gag gtc cgg gcc atc    2380
Arg Tyr Leu Ser Pro Asp Ala Thr Val Ser Thr Glu Val Arg Ala Ile
            735                 740                 745 att gcc tgg atg gag aag aac ccc ttc gtg ctg gga gca aat ctg aac    2428
Ile Ala Trp Met Glu Lys Asn Pro Phe Val Leu Gly Ala Asn Leu Asn
        750                 755                 760 ggc ggc gag cgg cta gta tcc tac ccc tac gat atg gcc cgc acg cct    2476
Gly Gly Glu Arg Leu Val Ser Tyr Pro Tyr Asp Met Ala Arg Thr Pro
    765                 770                 775 acc cag gag cag ctg ctg gcc gca gcc atg gca gca gcc cgg ggg gag    2524
Thr Gln Glu Gln Leu Leu Ala Ala Ala Met Ala Ala Ala Arg Gly Glu
780                 785                 790                 795 gat gag gac gag gtc tcc gag gcc cag gag act cca gac cac gcc atc    2572
Asp Glu Asp Glu Val Ser Glu Ala Gln Glu Thr Pro Asp His Ala Ile
                800                 805                 810 ttc cgg tgg ctt gcc atc tcc ttc gcc tcc gca cac ctc acc ttg acc    2620
Phe Arg Trp Leu Ala Ile Ser Phe Ala Ser Ala His Leu Thr Leu Thr
            815                 820                 825 gag ccc tac cgc gga ggc tgc caa gcc cag gac tac acc ggc ggc atg    2668
Glu Pro Tyr Arg Gly Gly Cys Gln Ala Gln Asp Tyr Thr Gly Gly Met
        830                 835                 840 ggc atc gtc aac ggg gcc aag tgg aac ccc cgg acc ggg act atc aat    2716
Gly Ile Val Asn Gly Ala Lys Trp Asn Pro Arg Thr Gly Thr Ile Asn
    845                 850                 855 gac ttc agt tac ctg cat acc aac tgc ctg gag ctc tcc ttc tac ctg    2764
Asp Phe Ser Tyr Leu His Thr Asn Cys Leu Glu Leu Ser Phe Tyr Leu
860                 865                 870                 875 ggc tgt gac aag ttc cct cat gag agt gag ctg ccc cgc gag tgg gag    2812
Gly Cys Asp Lys Phe Pro His Glu Ser Glu Leu Pro Arg Glu Trp Glu
                880                 885                 890 aac aac aag gag gcg ctg ctc acc ttc atg gag cag gtg cac cgc ggc    2860
Asn Asn Lys Glu Ala Leu Leu Thr Phe Met Glu Gln Val His Arg Gly
            895                 900                 905 att aag ggg gtg gtg acg gac gag caa ggc atc ccc att gcc aac gcc    2908
Ile Lys Gly Val Val Thr Asp Glu Gln Gly Ile Pro Ile Ala Asn Ala
        910                 915                 920 acc atc tct gtg agt ggc att aat cac ggc gtg aag aca gcc agt ggt    2956
Thr Ile Ser Val Ser Gly Ile Asn His Gly Val Lys Thr Ala Ser Gly
    925                 930                 935 ggt gat tac tgg cga atc ttg aac ccg ggt gag tac cgc gtg aca gcc    3004
Gly Asp Tyr Trp Arg Ile Leu Asn Pro Gly Glu Tyr Arg Val Thr Ala
940                 945                 950                 955 cac gcg gag ggc tac acc ccg agc gcc aag acc tgc aat gtt gac tat    3052
His Ala Glu Gly Tyr Thr Pro Ser Ala Lys Thr Cys Asn Val Asp Tyr
                960                 965                 970 gac atc ggg gcc act cag tgc aac ttc atc ctg gct cgc tcc aac tgg    3100
Asp Ile Gly Ala Thr Gln Cys Asn Phe Ile Leu Ala Arg Ser Asn Trp
```

-continued

| | | |
|---|---|---|
| aag cgc atc cgg gag atc atg gcc atg aac ggg aac cgg cct atc cca<br>Lys Arg Ile Arg Glu Ile Met Ala Met Asn Gly Asn Arg Pro Ile Pro<br>         990                       995                      1000 | 3148 | |
| cac ata gac cca tcg cgc cct atg acc ccc caa cag cga cgc ctg cag<br>His Ile Asp Pro Ser Arg Pro Met Thr Pro Gln Gln Arg Arg Leu Gln<br>   1005                     1010                     1015 | 3196 | |
| cag cga cgc cta caa cac cgc ctg cgg ctt cgg gca cag atg cgg ctg<br>Gln Arg Arg Leu Gln His Arg Leu Arg Leu Arg Ala Gln Met Arg Leu<br>1020                   1025                   1030                 1035 | 3244 | |
| cgg cgc ctc aac gcc acc acc acc cta ggc ccc cac act gtg cct ccc<br>Arg Arg Leu Asn Ala Thr Thr Thr Leu Gly Pro His Thr Val Pro Pro<br>         1040                     1045                   1050 | 3292 | |
| acg ctg ccc cct gcc cct gcc acc acc ctg agc act acc ata gag ccc<br>Thr Leu Pro Pro Ala Pro Ala Thr Thr Leu Ser Thr Thr Ile Glu Pro<br>   1055                     1060                     1065 | 3340 | |
| tgg ggc ctc ata ccg cca acc acc gct ggc tgg gag gag tcg gag act<br>Trp Gly Leu Ile Pro Pro Thr Thr Ala Gly Trp Glu Glu Ser Glu Thr<br>1070                   1075                   1080 | 3388 | |
| gag acc tac aca gag gtg gtg aca gag ttt ggg acc gag gtg gag ccc<br>Glu Thr Tyr Thr Glu Val Val Thr Glu Phe Gly Thr Glu Val Glu Pro<br>         1085                     1090                   1095 | 3436 | |
| gag ttt ggg acc aag gtg gag ccc gag ttt gag acc cag ttg gag cct<br>Glu Phe Gly Thr Lys Val Glu Pro Glu Phe Glu Thr Gln Leu Glu Pro<br>1100                   1105                   1110                 1115 | 3484 | |
| gag ttc gag acc cag ctg gaa ccc gag ttt gag gaa gag gag gag gag<br>Glu Phe Glu Thr Gln Leu Glu Pro Glu Phe Glu Glu Glu Glu Glu Glu<br>                   1120                     1125                   1130 | 3532 | |
| gag aaa gag gag gag ata gcc act ggc cag gca ttc ccc ttc aca aca<br>Glu Lys Glu Glu Glu Ile Ala Thr Gly Gln Ala Phe Pro Phe Thr Thr<br>               1135                     1140                   1145 | 3580 | |
| gta gag acc tac aca gtg aac ttt ggg gac ttc tgagatcagc gtcctaccaa<br>Val Glu Thr Tyr Thr Val Asn Phe Gly Asp Phe<br>         1150                     1155 | 3633 | |
| gaccccagcc caactcaagc tacagcagca gcacttccca agcctgctga ccacagtcac | 3693 | |
| atcacccatc agcacatgga aggcccctgg tatggacact gaaaggaagg gctggtcctg | 3753 | |
| ccccctttgag ggggtgcaaa catgactggg acctaagagc cagaggctgt gtagaggctc | 3813 | |
| ctgctccacc tgccagtctc gtaagagatg gggttgctgc agtgttggag taggggcaga | 3873 | |
| gggagggagc caaggtcact ccaataaaac aagctcatgg caaaaaaaaa aaaaaaaaa | 3933 | |
| aa | 3935 | |

<210> SEQ ID NO 2
<211> LENGTH: 1158
<212> TYPE: PRT
<213> ORGANISM: Homo sapiens

<400> SEQUENCE: 2

Met Ala Ala Val Arg Gly Ala Pro Leu Leu Ser Cys Leu Leu Ala Leu
  1               5                  10                  15

Leu Ala Leu Cys Pro Gly Gly Arg Pro Gln Thr Val Leu Thr Asp Asp
             20                  25                  30

Glu Ile Glu Glu Phe Leu Glu Gly Phe Leu Ser Glu Leu Glu Pro Glu
         35                  40                  45

Pro Arg Glu Asp Asp Val Glu Ala Pro Pro Pro Glu Pro Thr Pro
     50                  55                  60

Arg Val Arg Lys Ala Gln Ala Gly Gly Lys Pro Gly Lys Arg Pro Gly

-continued

```
            65                  70                  75                  80
Thr Ala Ala Glu Val Pro Pro Glu Lys Thr Lys Asp Lys Gly Lys Lys
                    85                  90                  95
Gly Lys Lys Asp Lys Gly Pro Lys Val Pro Lys Glu Ser Leu Glu Gly
                100                 105                 110
Ser Pro Arg Pro Pro Lys Lys Gly Lys Glu Lys Pro Pro Lys Ala Thr
            115                 120                 125
Lys Lys Pro Lys Glu Lys Pro Pro Lys Ala Thr Lys Lys Pro Lys Glu
        130                 135                 140
Glu Pro Pro Lys Ala Thr Lys Lys Pro Lys Glu Lys Pro Pro Lys Ala
145                 150                 155                 160
Thr Lys Lys Pro Pro Ser Gly Lys Arg Pro Pro Ile Leu Ala Pro Ser
                165                 170                 175
Glu Thr Leu Glu Trp Pro Leu Pro Pro Ser Pro Gly Pro Glu
                180                 185                 190
Glu Leu Pro Gln Glu Gly Gly Ala Pro Leu Ser Asn Asn Trp Gln Asn
            195                 200                 205
Pro Gly Glu Glu Thr His Val Glu Ala Gln Glu His Gln Pro Glu Pro
        210                 215                 220
Glu Glu Glu Thr Glu Gln Pro Thr Leu Asp Tyr Asn Asp Gln Ile Glu
225                 230                 235                 240
Arg Glu Asp Tyr Glu Asp Phe Glu Tyr Ile Arg Arg Gln Lys Gln Pro
                245                 250                 255
Arg Pro Pro Ser Arg Arg Arg Pro Glu Arg Val Trp Pro Glu
                260                 265                 270
Pro Pro Glu Glu Lys Ala Pro Ala Pro Ala Pro Glu Glu Arg Ile Glu
            275                 280                 285
Pro Pro Val Lys Pro Leu Leu Pro Pro Leu Pro Pro Asp Tyr Gly Asp
        290                 295                 300
Gly Tyr Val Ile Pro Asn Tyr Asp Asp Met Asp Tyr Tyr Phe Gly Pro
305                 310                 315                 320
Pro Pro Pro Gln Lys Pro Asp Ala Glu Arg Gln Thr Asp Glu Glu Lys
                325                 330                 335
Glu Glu Leu Lys Lys Pro Lys Lys Glu Asp Ser Ser Pro Lys Glu Glu
            340                 345                 350
Thr Asp Lys Trp Ala Val Glu Lys Gly Lys Asp His Lys Glu Pro Arg
        355                 360                 365
Lys Gly Glu Glu Leu Glu Glu Trp Thr Pro Thr Glu Lys Val Lys
    370                 375                 380
Cys Pro Pro Ile Gly Met Glu Ser His Arg Ile Glu Asp Asn Gln Ile
385                 390                 395                 400
Arg Ala Ser Ser Met Leu Arg His Gly Leu Gly Ala Gln Arg Gly Arg
                405                 410                 415
Leu Asn Met Gln Thr Gly Ala Thr Glu Asp Asp Tyr Tyr Asp Gly Ala
            420                 425                 430
Trp Cys Ala Glu Asp Asp Ala Arg Thr Gln Trp Ile Glu Val Asp Thr
        435                 440                 445
Arg Arg Thr Thr Arg Phe Thr Gly Val Ile Thr Gln Gly Arg Asp Ser
    450                 455                 460
Ser Ile His Asp Asp Phe Val Thr Phe Phe Val Gly Phe Ser Asn
465                 470                 475                 480
Asp Ser Gln Thr Trp Val Met Tyr Thr Asn Gly Tyr Glu Glu Met Thr
                485                 490                 495
```

```
Phe His Gly Asn Val Asp Lys Asp Thr Pro Val Leu Ser Glu Leu Pro
            500                 505                 510
Glu Pro Val Val Ala Arg Phe Ile Arg Ile Tyr Pro Leu Thr Trp Asn
        515                 520                 525
Gly Ser Leu Cys Met Arg Leu Glu Val Leu Gly Cys Ser Val Ala Pro
        530                 535                 540
Val Tyr Ser Tyr Tyr Ala Gln Asn Glu Val Val Ala Thr Asp Asp Leu
545                 550                 555                 560
Asp Phe Arg His His Ser Tyr Lys Asp Met Arg Gln Leu Met Lys Val
                565                 570                 575
Val Asn Glu Glu Cys Pro Thr Ile Thr Arg Thr Tyr Ser Leu Gly Lys
            580                 585                 590
Ser Ser Arg Gly Leu Lys Ile Tyr Ala Met Glu Ile Ser Asp Asn Pro
        595                 600                 605
Gly Glu His Glu Leu Gly Glu Pro Glu Phe Arg Tyr Thr Ala Gly Ile
        610                 615                 620
His Gly Asn Glu Val Leu Gly Arg Glu Leu Leu Leu Leu Met Gln
625                 630                 635                 640
Tyr Leu Cys Arg Glu Tyr Arg Asp Gly Asn Pro Arg Val Arg Ser Leu
                645                 650                 655
Val Gln Asp Thr Arg Ile His Leu Val Pro Ser Leu Asn Pro Asp Gly
            660                 665                 670
Tyr Glu Val Ala Ala Gln Met Gly Ser Glu Phe Gly Asn Trp Ala Leu
        675                 680                 685
Gly Leu Trp Thr Glu Gly Phe Asp Ile Phe Glu Asp Phe Pro Asp
        690                 695                 700
Leu Asn Ser Val Leu Trp Gly Ala Glu Glu Arg Lys Trp Val Pro Tyr
705                 710                 715                 720
Arg Val Pro Asn Asn Leu Pro Ile Pro Glu Arg Tyr Leu Ser Pro
                725                 730                 735
Asp Ala Thr Val Ser Thr Glu Val Arg Ala Ile Ile Ala Trp Met Glu
            740                 745                 750
Lys Asn Pro Phe Val Leu Gly Ala Asn Leu Asn Gly Gly Glu Arg Leu
        755                 760                 765
Val Ser Tyr Pro Tyr Asp Met Ala Arg Thr Pro Thr Gln Glu Gln Leu
        770                 775                 780
Leu Ala Ala Met Ala Ala Ala Arg Gly Glu Asp Glu Asp Glu Val
785                 790                 795                 800
Ser Glu Ala Gln Glu Thr Pro Asp His Ala Ile Phe Arg Trp Leu Ala
                805                 810                 815
Ile Ser Phe Ala Ser Ala His Leu Thr Leu Thr Glu Pro Tyr Arg Gly
            820                 825                 830
Gly Cys Gln Ala Gln Asp Tyr Thr Gly Gly Met Gly Ile Val Asn Gly
        835                 840                 845
Ala Lys Trp Asn Pro Arg Thr Gly Thr Ile Asn Asp Phe Ser Tyr Leu
        850                 855                 860
His Thr Asn Cys Leu Glu Leu Ser Phe Tyr Leu Gly Cys Asp Lys Phe
865                 870                 875                 880
Pro His Glu Ser Glu Leu Pro Arg Glu Trp Asn Asn Lys Glu Ala
                885                 890                 895
Leu Leu Thr Phe Met Glu Gln Val His Arg Gly Ile Lys Gly Val Val
            900                 905                 910
```

```
Thr Asp Glu Gln Gly Ile Pro Ile Ala Asn Ala Thr Ile Ser Val Ser
        915                 920                 925

Gly Ile Asn His Gly Val Lys Thr Ala Ser Gly Gly Asp Tyr Trp Arg
    930                 935                 940

Ile Leu Asn Pro Gly Glu Tyr Arg Val Thr Ala His Ala Glu Gly Tyr
945                 950                 955                 960

Thr Pro Ser Ala Lys Thr Cys Asn Val Asp Tyr Asp Ile Gly Ala Thr
                965                 970                 975

Gln Cys Asn Phe Ile Leu Ala Arg Ser Asn Trp Lys Arg Ile Arg Glu
            980                 985                 990

Ile Met Ala Met Asn Gly Asn Arg Pro Ile Pro His Ile Asp Pro Ser
        995                 1000                1005

Arg Pro Met Thr Pro Gln Gln Arg Arg Leu Gln Gln Arg Arg Leu Gln
    1010                1015                1020

His Arg Leu Arg Leu Arg Ala Gln Met Arg Leu Arg Arg Leu Asn Ala
1025                1030                1035                1040

Thr Thr Thr Leu Gly Pro His Thr Val Pro Pro Thr Leu Pro Pro Ala
            1045                1050                1055

Pro Ala Thr Thr Leu Ser Thr Thr Ile Glu Pro Trp Gly Leu Ile Pro
        1060                1065                1070

Pro Thr Thr Ala Gly Trp Glu Glu Ser Glu Thr Glu Thr Tyr Thr Glu
            1075                1080                1085

Val Val Thr Glu Phe Gly Thr Glu Val Glu Pro Glu Phe Gly Thr Lys
        1090                1095                1100

Val Glu Pro Glu Phe Glu Thr Gln Leu Glu Pro Glu Phe Glu Thr Gln
1105                1110                1115                1120

Leu Glu Pro Glu Phe Glu Glu Glu Glu Glu Lys Glu Glu
            1125                1130                1135

Ile Ala Thr Gly Gln Ala Phe Pro Phe Thr Thr Val Glu Thr Tyr Thr
                1140                1145                1150

Val Asn Phe Gly Asp Phe
        1155

<210> SEQ ID NO 3
<211> LENGTH: 2743
<212> TYPE: DNA
<213> ORGANISM: Mus musculus

<400> SEQUENCE: 3
aagcttagtc tccctctctc ctggctcctc tcctggggct tccctatgga ggtagcactt     60
acagaagatg cttgttccaa accttcaggg gtacaaacta cacagatata ctgaaggaca    120
ggaggctggg gcctcccccc accccaaca gccactgttc tctcaggagc tctgcttctg     180
ctctgcagca ttgaaaacaa aactgaagga caccttcctt ctctcaggcc agcccagtgc    240
tgttgtgtga tccctcggga agactctaac gcattcacag ggacaacagg agttgggagg    300
gagaggagtt acagaacttt ccagcaggac ctcaggagaa cgcctggaca cggacaggaa    360
cccccaaccc ctcagggacc cccttggacc ctttgagtgc tcctgatcat ggaagccacc    420
agcctcccga ttcctcagct gtggccttgg cagtgccctc tggacatttg acttaaacgc    480
tatgctcttc agcagagtgg agagctctcc tcacaggctc tggcttctgg ttgtcctctt    540
gccccagcgc tgtgggccca ggttagaaag acttcctgag acaggctcc ctcaggagga      600 tccccagcgt acgactgtgc tcccacgcac ctttccggat tttctgtgtg gaggcctcaa    660
cccctcaggc ctcctgggcc agctcctctg ctcgaattcc tgtccgtgac tcattgaggc    720
```

```
tcaggaaaag gctttctaga ccttaggttt ctttgttttc cattttgaa atggcttctg       780 tttcccctgg cagagaatat ccaacccaaa ttcagtccaa gtatgaccca tgcctaggga       840
agtgacatcc atgtcccctc atgcaccctg tggcataccc agcatgacac actggaccag       900
actgggggca cggaagccaa ttcccagaac tgactttgag cacaatgatt cagagggtga       960
ccatgagtga gacttgcttt actcttgctc tgcgaccagg ttgaagtctc tcatggggag      1020
gcctagctgt gagaggattg tcctgggatg ggggaagggg gagcaaagtg gatgaggacc      1080
aacagcctgt gggatgcaag ggctgatcgt gtgtgctagg cacagcacaa agtggtccat      1140
ttagccgggc agtggtggtg cacaccttta atcccagcac ttgggaggca gcagcaggtg      1200
ggtttctgag ttcgaggcca gcctggtcta cagagcaagt tccaggacag ccagagctac      1260
acagagaaac tctgtctcaa aaaatcgaa taaaccagaa aggtggtcca tttaatatgc       1320
gtatagtaag ttgtggacac gggagttccc ctgctgagtc agacagctag gagggctaag      1380
atgggttaga ccctccccc ccccacacac acacacacac actcacacac acatcagttc       1440
ttggcatagt ctccatgctt cctcaaggag agccagaaag gagactgccg ggaggagctt      1500
gcctactccc tgagagcagt gggttacaga gcccagtgcc cgaaaatttc ccttttctct      1560
ccctgctcat gctggacaga gagggtgagg gtgagggtga agactgagg aggtggcatc       1620 gtgttggtgt ttcttgacct gctttttctt ttttctcttc cagctgagat gtaaactttc      1680
ccatgtcaat catctggggg tcgctattct tttttatcag agtgcctccc caccttggtt      1740
gaaagctgcc tgccactacc ctggacctat ggctgctaca agcccacgtt cacatcttta      1800
atccttcatg ggtaaatgct ctggcattcc tgggcttagc tatgatggcc attatgagcc      1860
agccaacgtt tgtattctag aagccatagc tgaagctgtt gtaaacaatt tgttgtttta      1920
accgcttctg gtcagaggaa ggagagaata gctattactc cacattggga cctgagccct      1980
gagctctgaa gtgggctcc tatctccata aggacagcag cttgctgaga acagcttttc       2040
acagccttcc tcgcaaaaat tggctccaaa gacctggat gttggtgata actggacaaa       2100
ggtgacacct gtgcaagcac acagcaggtg acactttgaa gagctaacct ccagaaagtg      2160
gaaaggaggt gatcgccagt accctcgagg gccctactcc ctccctcccc tagcaatctc      2220
cctgggctca gagcaaaggg cacagcgggt tagagcacag gtctccttag actccgcaca      2280
ctcccttccc cataactgtt gcattctttt ctcccaggcc ttcctccccg ctaggcgccc      2340
tgcacccaga ccctctaaac tggcgcgtga cgctgctatt agtctgggct ccgtgctgtc      2400
cgcctccctc ccccgcagcc cccggtccaa ggccggctcc tcctcctccc cctccggaaa      2460
cccgaagccc ccgccccggc caggccgtcg caagcgctct ggagggcggt ccgcgtgaga      2520
gccagccacg cggggcagga gcgcccagtt gctgccggag ctgggcccgc cagaacctct      2580
cctggagccc cttgctctcc ttgaatctcc ctttcccacc gctttctgga tacccttgac      2640
gcccacgttc ctcgcgccct ttcccgcccc tacgcgggc gctgcccctg ccacccaagt       2700
ccctgctcaa gcccgcccgg tcccgcgcgt gcccagagcc atg                        2743
```

<210> SEQ ID NO 4
<211> LENGTH: 17
<212> TYPE: DNA
<213> ORGANISM: Mus musculus

<400> SEQUENCE: 4
atctggttgt cctcaat                                                       17

<210> SEQ ID NO 5
<211> LENGTH: 17
<212> TYPE: DNA
<213> ORGANISM: Mus musculus

<400> SEQUENCE: 5
tgactccatc ccaatag                                                    17

<210> SEQ ID NO 6
<211> LENGTH: 26
<212> TYPE: DNA
<213> ORGANISM: Mus musculus

<400> SEQUENCE: 6
cggaattcag tccctgctca agcccg                                          26

<210> SEQ ID NO 7
<211> LENGTH: 28
<212> TYPE: DNA
<213> ORGANISM: Mus musculus

<400> SEQUENCE: 7
cgaagcttga agtccccaaa gttcactg                                        28

<210> SEQ ID NO 8
<211> LENGTH: 1128
<212> TYPE: PRT
<213> ORGANISM: Mus musculus

<400> SEQUENCE: 8

Met Ala Pro Val Arg Thr Ala Ser Leu Leu Cys Gly Leu Leu Ala Leu
1               5                   10                  15

Leu Thr Leu Cys Pro Glu Gly Asn Pro Gln Thr Val Leu Thr Asp Asp
            20                  25                  30

Glu Ile Glu Glu Phe Leu Glu Gly Phe Leu Ser Glu Leu Glu Thr Gln
        35                  40                  45

Ser Pro Pro Arg Glu Asp Asp Val Glu Val Gln Pro Leu Pro Glu Pro
    50                  55                  60

Thr Gln Arg Pro Arg Lys Ser Lys Ala Gly Gly Lys Gln Arg Ala Asp
65                  70                  75                  80

Val Glu Val Pro Pro Glu Lys Asn Lys Asp Lys Glu Lys Lys Gly Lys
                85                  90                  95

Lys Asp Lys Gly Pro Lys Ala Thr Lys Pro Leu Glu Gly Ser Thr Arg
            100                 105                 110

Pro Thr Lys Lys Pro Lys Glu Lys Pro Pro Lys Ala Thr Lys Lys Pro
        115                 120                 125

Lys Glu Lys Pro Pro Lys Ala Thr Lys Pro Lys Glu Lys Pro Pro
    130                 135                 140

Lys Ala Thr Lys Lys Pro Lys Glu Lys Pro Pro Lys Ala Thr Lys Arg
145                 150                 155                 160

Pro Ser Ala Gly Lys Lys Phe Ser Thr Val Ala Pro Leu Glu Thr Leu
                165                 170                 175

Asp Arg Leu Leu Pro Ser Pro Ser Asn Pro Ser Ala Gln Glu Leu Pro
            180                 185                 190

Gln Lys Arg Asp Thr Pro Phe Pro Asn Ala Trp Gln Gly Gln Gly Glu
        195                 200                 205

Glu Thr Gln Val Glu Ala Lys Gln Pro Arg Pro Glu Pro Glu Glu Glu
    210                 215                 220

-continued

```
Thr Glu Met Pro Thr Leu Asp Tyr Asn Asp Gln Ile Glu Lys Glu Asp
225                 230                 235                 240

Tyr Glu Asp Phe Glu Tyr Ile Arg Arg Gln Lys Gln Pro Arg Pro Thr
            245                 250                 255

Pro Ser Arg Arg Arg Leu Trp Pro Glu Arg Pro Glu Glu Lys Thr Glu
                260                 265                 270

Glu Pro Glu Glu Arg Lys Glu Val Glu Pro Leu Lys Pro Leu Leu
        275                 280                 285

Pro Pro Asp Tyr Gly Asp Ser Tyr Val Ile Pro Asn Tyr Asp Asp Leu
    290                 295                 300

Asp Tyr Tyr Phe Pro His Pro Pro Gln Lys Pro Asp Val Gly Gln
305                 310                 315                 320

Glu Val Asp Glu Glu Lys Glu Met Lys Lys Pro Lys Lys Glu Gly
                325                 330                 335

Ser Ser Pro Lys Glu Asp Thr Glu Asp Lys Trp Thr Val Glu Lys Asn
                340                 345                 350

Lys Asp His Lys Gly Pro Arg Lys Gly Glu Leu Glu Glu Glu Trp
        355                 360                 365

Ala Pro Val Glu Lys Ile Lys Cys Pro Pro Ile Gly Met Glu Ser His
370                 375                 380

Arg Ile Glu Asp Asn Gln Ile Arg Ala Ser Ser Met Leu Arg His Gly
385                 390                 395                 400

Leu Gly Ala Gln Arg Gly Arg Leu Asn Met Gln Ala Gly Ala Asn Glu
            405                 410                 415

Asp Asp Tyr Tyr Asp Gly Ala Trp Cys Ala Glu Asp Glu Ser Gln Thr
            420                 425                 430

Gln Trp Ile Glu Val Asp Thr Arg Arg Thr Thr Arg Phe Thr Gly Val
        435                 440                 445

Ile Thr Gln Gly Arg Asp Ser Ser Ile His Asp Asp Phe Val Thr Thr
450                 455                 460

Phe Phe Val Gly Phe Ser Asn Asp Ser Gln Thr Trp Val Met Tyr Thr
465                 470                 475                 480

Asn Gly Tyr Glu Glu Met Thr Phe Tyr Gly Asn Val Asp Lys Asp Thr
                485                 490                 495

Pro Val Leu Ser Glu Leu Pro Glu Pro Val Val Ala Arg Phe Ile Arg
        500                 505                 510

Ile Tyr Pro Leu Thr Trp Asn Gly Ser Leu Cys Met Arg Leu Glu Val
        515                 520                 525

Leu Gly Cys Pro Val Thr Pro Val Tyr Ser Tyr Tyr Ala Gln Asn Glu
    530                 535                 540

Val Val Thr Thr Asp Ser Leu Asp Phe Arg His His Ser Tyr Lys Asp
545                 550                 555                 560

Met Arg Gln Leu Met Lys Ala Val Asn Glu Glu Cys Pro Thr Ile Thr
                565                 570                 575

Arg Thr Tyr Ser Leu Gly Lys Ser Ser Arg Gly Leu Lys Ile Tyr Ala
            580                 585                 590

Met Glu Ile Ser Asp Asn Pro Gly Asp His Glu Leu Gly Glu Pro Glu
        595                 600                 605

Phe Arg Tyr Thr Ala Gly Ile His Gly Asn Glu Val Leu Gly Arg Glu
    610                 615                 620

Leu Leu Leu Leu Leu Met Gln Tyr Leu Cys Gln Glu Tyr Arg Asp Gly
625                 630                 635                 640
```

-continued

```
Asn Pro Arg Val Arg Asn Leu Val Gln Asp Thr Arg Ile His Leu Val
            645                 650                 655
Pro Ser Leu Asn Pro Asp Gly Tyr Glu Val Ala Ala Gln Met Gly Ser
        660                 665                 670
Glu Phe Gly Asn Trp Ala Leu Gly Leu Trp Thr Glu Glu Gly Phe Asp
    675                 680                 685
Ile Phe Glu Asp Phe Pro Asp Leu Asn Ser Val Leu Trp Ala Ala Glu
690                 695                 700
Glu Lys Lys Trp Val Pro Tyr Arg Val Pro Asn Asn Asn Leu Pro Ile
705                 710                 715                 720
Pro Glu Arg Tyr Leu Ser Pro Asp Ala Thr Val Ser Thr Glu Val Arg
                725                 730                 735
Ala Ile Ile Ser Trp Met Glu Lys Asn Pro Phe Val Leu Gly Ala Asn
            740                 745                 750
Leu Asn Gly Gly Glu Arg Leu Val Ser Tyr Pro Tyr Asp Met Ala Arg
        755                 760                 765
Thr Pro Ser Gln Glu Gln Leu Leu Ala Glu Ala Leu Ala Ala Ala Arg
    770                 775                 780
Gly Glu Asp Asp Gly Val Ser Glu Ala Gln Glu Thr Pro Asp His
785                 790                 795                 800
Ala Ile Phe Arg Trp Leu Ala Ile Ser Phe Ala Ser Ala His Leu Thr
                805                 810                 815
Met Thr Glu Pro Tyr Arg Gly Gly Cys Gln Ala Gln Asp Tyr Thr Ser
            820                 825                 830
Gly Met Gly Ile Val Asn Gly Ala Lys Trp Asn Pro Arg Ser Gly Thr
        835                 840                 845
Phe Asn Arg Phe Ser Tyr Leu His Thr Asn Cys Leu Glu Leu Ser Val
    850                 855                 860
Tyr Leu Gly Cys Asp Lys Phe Pro His Glu Ser Glu Leu Pro Arg Glu
865                 870                 875                 880
Trp Glu Asn Asn Lys Glu Ala Leu Leu Thr Phe Met Glu Gln Val His
                885                 890                 895
Arg Gly Ile Lys Gly Val Val Thr Asp Glu Gln Gly Ile Pro Ile Ala
            900                 905                 910
Asn Ala Thr Ile Ser Val Ser Gly Ile Asn His Gly Val Lys Thr Ala
        915                 920                 925
Ser Gly Gly Asp Tyr Trp Arg Ile Leu Asn Pro Gly Glu Tyr Arg Val
    930                 935                 940
Thr Ala His Ala Glu Gly Tyr Thr Ser Ser Ala Lys Ile Cys Asn Val
945                 950                 955                 960
Asp Tyr Asp Ile Gly Ala Thr Gln Cys Asn Phe Ile Leu Ala Arg Ser
                965                 970                 975
Asn Trp Lys Arg Ile Arg Glu Ile Leu Ala Met Asn Gly Asn Arg Pro
            980                 985                 990
Ile Leu Gly Val Asp Pro Ser Arg Pro Met Thr Pro Gln Gln Arg Arg
        995                 1000                1005
Met Gln Gln Arg Arg Leu Gln Tyr Arg Leu Arg Met Arg Glu Gln Met
    1010                1015                1020
Arg Leu Arg Arg Leu Asn Ser Thr Ala Gly Pro Ala Thr Ser Pro Thr
1025                1030                1035                1040
Pro Ala Leu Met Pro Pro Pro Ser Pro Thr Pro Ala Ile Thr Leu Arg
                1045                1050                1055
Pro Trp Glu Val Leu Pro Thr Thr Thr Ala Gly Trp Glu Glu Ser Glu
```

-continued

```
                1060                    1065                    1070
Thr Glu Thr Tyr Thr Glu Val Val Thr Glu Phe Glu Thr Glu Tyr Gly
        1075                    1080                    1085

Thr Asp Leu Glu Val Glu Glu Ile Glu Glu Glu Glu Glu Glu Glu
        1090                    1095                    1100

Glu Glu Met Asp Thr Gly Leu Thr Phe Pro Leu Thr Thr Val Glu Thr
1105                    1110                    1115                    1120

Tyr Thr Val Asn Phe Gly Asp Phe
                1125
```